(12) United States Patent
Couture et al.

(10) Patent No.: US 11,849,957 B2
(45) Date of Patent: Dec. 26, 2023

(54) PATIENT-SPECIFIC INSTRUMENTATION AND METHOD FOR ARTICULAR JOINT REPAIR

(71) Applicant: ZIMMER, INC., Warsaw, IN (US)

(72) Inventors: Pierre Couture, Montreal (CA); Trong Tin Nguyen, Laval (CA); Anselm Jakob Neurohr, Montreal (CA); Jean-Sebastien Merette, Mont-St-Hilaire (CA); Jean-Guillaume Abiven, Montreal (CA); Alain Richard, Lachine (CA)

(73) Assignee: ZIMMER, INC., Warsaw, IN (US)

( * ) Notice: Subject to any disclaimer, the term of this patent is extended or adjusted under 35 U.S.C. 154(b) by 174 days.

(21) Appl. No.: 16/403,843

(22) Filed: May 6, 2019

(65) Prior Publication Data

US 2019/0254681 A1 Aug. 22, 2019

Related U.S. Application Data

(63) Continuation of application No. 13/902,219, filed on May 24, 2013, now Pat. No. 10,327,786.
(Continued)

(51) Int. Cl.
*A61B 17/15* (2006.01)
*A61F 2/46* (2006.01)
*A61B 34/10* (2016.01)

(52) U.S. Cl.
CPC .......... *A61B 17/154* (2013.01); *A61B 17/155* (2013.01); *A61B 17/157* (2013.01); *A61B 2034/108* (2016.02); *A61F 2002/4658* (2013.01)

(58) Field of Classification Search
CPC ..... A61B 17/15; A61B 17/154; A61B 17/155; A61B 17/157; A61B 17/158; A61B 17/17; A61B 17/1764
(Continued)

(56) References Cited

U.S. PATENT DOCUMENTS 4,564,732 A * 1/1986 Lancaster ............ H01H 13/807
 403/381
4,841,975 A 6/1989 Woolson
(Continued)

FOREIGN PATENT DOCUMENTS

AU 2004293091 A1 6/2005
AU 2004293104 A1 6/2005
(Continued)

OTHER PUBLICATIONS

Hofmann et al, "Natural-Knee II System", Intermedics Orthopedics, Austin, TX, 1995.

*Primary Examiner* — Si Ming Ku
(74) *Attorney, Agent, or Firm* — NORTON ROSE FULBRIGHT CANADA LLP

(57) ABSTRACT

Patient-specific instrumentation for use when performing articular joint repair is provided. A patient-specific jig is adapted to be positioned over a bone at an articular surface thereof for assisting in preparing the bone surface for reception of a prosthesis. The jig comprises a bone contacting portion adapted to matingly contact a portion of the articular surface of the bone and a cutting slot adapted to receive therein a saw blade for resecting the articular surface of the bone. The cutting slot may be press-fitted into the opening of a cut guide. A patient-specific plate and a patient-specific rotational guide are also provided for guid-
(Continued)

ing a positioning of the prosthesis over the resected surface of the bone. A method for manufacturing the patient-specific jig is further provided.

17 Claims, 31 Drawing Sheets

Related U.S. Application Data

(60) Provisional application No. 61/787,579, filed on Mar. 15, 2013, provisional application No. 61/671,990, filed on Jul. 16, 2012, provisional application No. 61/651,061, filed on May 24, 2012.

(58) Field of Classification Search
USPC .......................................................... 606/88
See application file for complete search history.

(56) References Cited

U.S. PATENT DOCUMENTS

| | | | |
|---|---|---|---|
| 5,098,383 A | 3/1992 | Hemmy et al. | |
| 5,490,854 A | 2/1996 | Fisher et al. | |
| 5,768,134 A | 6/1998 | Swaelens et al. | |
| 5,871,018 A | 2/1999 | Delp et al. | |
| 5,916,219 A | 6/1999 | Matsuno et al. | |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 | 5/2009 | Burdulis | |
| 7,618,451 B2 | 11/2009 | Berez et al. | |
| 7,634,119 B2 | 12/2009 | Tsougarakis et al. | |
| 7,717,956 B2 | 5/2010 | Lang | |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,585,708 B2 | 9/2013 | Fitz et al. | |
| 8,545,569 B2 | 10/2013 | Fitz et al. | |
| 8,551,099 B2 | 10/2013 | Lang | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 2003/0055502 A1 | 3/2003 | Lang et al. | |
| 2003/0216669 A1 | 11/2003 | Lang et al. | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0204644 A1 | 10/2004 | Tsougarakis et al. | |
| 2004/0204760 A1 | 10/2004 | Fitz et al. | |
| 2004/0236424 A1 | 11/2004 | Berez et al. | |
| 2005/0228393 A1* | 10/2005 | Williams, III | A61B 17/155 606/87 |
| 2005/0234461 A1 | 10/2005 | Burdulis et al. | |
| 2005/0267584 A1 | 12/2005 | Burdulis et al. | |
| 2006/0111722 A1 | 5/2006 | Bouadi | |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0198022 A1 | 8/2007 | Lang et al. | |
| 2007/0226986 A1 | 10/2007 | Park et al. | |
| 2007/0233141 A1 | 10/2007 | Park | |
| 2007/0233269 A1 | 10/2007 | Steines et al. | |
| 2007/0250169 A1 | 10/2007 | Lang | |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0195216 A1 | 8/2008 | Philipp | |
| 2008/0243127 A1 | 10/2008 | Lang et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1 | 11/2008 | Kunz et al. | |
| 2009/0024131 A1 | 1/2009 | Metzgu et al. | |
| 2009/0087276 A1* | 4/2009 | Rose | A61B 17/155 409/79 |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0110498 A1 | 4/2009 | Park et al. | |
| 2009/0131941 A1 | 5/2009 | Park et al. | |
| 2009/0131942 A1 | 5/2009 | Aker et al. | |
| 2009/0138020 A1 | 5/2009 | Park et al. | |
| 2009/0157083 A1 | 6/2009 | Park et al. | |
| 2009/0222014 A1 | 9/2009 | Bojarski et al. | |
| 2009/0222016 A1 | 9/2009 | Park et al. | |
| 2009/0222103 A1 | 9/2009 | Fitz et al. | |
| 2009/0226068 A1 | 9/2009 | Fitz et al. | |
| 2009/0228113 A1 | 9/2009 | Lang et al. | |
| 2009/0254093 A1 | 10/2009 | White et al. | |
| 2009/0270868 A1 | 10/2009 | Park et al. | |
| 2009/0276045 A1 | 11/2009 | Lang | |
| 2009/0306676 A1 | 12/2009 | Lang et al. | |
| 2009/0307893 A1 | 12/2009 | Burdulis, Jr. et al. | |
| 2009/0312805 A1 | 12/2009 | Lang et al. | |
| 2010/0023015 A1 | 1/2010 | Park | |
| 2010/0042105 A1 | 2/2010 | Park et al. | |

(56) References Cited

U.S. PATENT DOCUMENTS

| | | |
|---|---|---|
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Michael et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1* | 7/2011 | Dubeau ............... A61B 17/151 606/87 |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds |
| 2011/0257653 A1 | 10/2011 | Hughes et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116410 A1 | 5/2012 | Kortenbach |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271314 A1* | 10/2012 | Stemniski ............ A61B 17/1775 606/87 |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0006251 A1* | 1/2013 | Aram ................ A61B 17/1721 606/88 |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |

(56) References Cited

U.S. PATENT DOCUMENTS

| | | | |
|---|---|---|---|
| 2013/0211409 A1 | 8/2013 | Burdulis, Jr. et al. | |
| 2013/0211410 A1 | 8/2013 | Landes et al. | |
| 2013/0211531 A1 | 8/2013 | Steines et al. | |
| 2013/0245803 A1 | 9/2013 | Lang | |
| 2013/0253522 A1 | 9/2013 | Bojarski et al. | |
| 2013/0289570 A1 | 10/2013 | Chao | |
| 2013/0296871 A1* | 11/2013 | Lazar | A61B 17/15 606/87 |
| 2013/0296874 A1 | 11/2013 | Chao | |
| 2013/0297031 A1 | 11/2013 | Hafez | |
| 2013/0317511 A1 | 11/2013 | Bojarski et al. | |
| 2013/0331850 A1 | 12/2013 | Bojarski et al. | |
| 2014/0005792 A1 | 1/2014 | Lang et al. | |
| 2014/0029814 A1 | 1/2014 | Fitz et al. | |
| 2014/0031826 A1 | 1/2014 | Bojarski et al. | |
| 2014/0039631 A1 | 2/2014 | Bojarski et al. | |
| 2014/0058396 A1 | 2/2014 | Fitz et al. | |
| 2014/0058397 A1 | 2/2014 | Fitz et al. | |
| 2014/0066935 A1 | 3/2014 | Fitz et al. | |
| 2014/0066936 A1 | 3/2014 | Fitz et al. | |
| 2014/0074441 A1 | 3/2014 | Fitz et al. | |
| 2014/0086780 A1 | 3/2014 | Miller et al. | |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 2237894 Y | 10/1996 |
| CN | 2491539 Y | 5/2002 |
| CN | 1418073 A | 5/2003 |
| CN | 1433111 A | 7/2003 |
| CN | 1728976 A | 2/2006 |
| CN | 1729483 A | 2/2006 |
| CN | 1729484 A | 2/2006 |
| CN | 1913844 A | 2/2007 |
| CN | 2914386 Y | 6/2007 |
| CN | 101111197 A | 1/2008 |
| CN | 101384230 A | 3/2009 |
| CN | 101442960 A | 5/2009 |
| CN | 100502808 C | 6/2009 |
| CN | 101588761 A | 11/2009 |
| CN | 101790353 A | 7/2010 |
| CN | 102006841 A | 4/2011 |
| CN | 102125448 A | 7/2011 |
| CN | 201954376 U | 8/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 | 3/2011 |
| DE | 60239674 | 5/2011 |
| DE | 602004032166 | 5/2011 |
| DE | 602005027391 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |

(56) References Cited

FOREIGN PATENT DOCUMENTS

| | | | |
|---|---|---|---|
| EP | 2671521 | A3 | 12/2013 |
| EP | 2671522 | A3 | 12/2013 |
| EP | 2114312 | B1 | 1/2014 |
| EP | 2710967 | A2 | 3/2014 |
| GB | 2484042 | A | 3/2012 |
| GB | 2489884 | A | 10/2012 |
| GB | 201213674 | | 10/2012 |
| GB | 2484042 | B | 3/2014 |
| HK | 1059882 | A1 | 8/2011 |
| HK | 1072710 | A1 | 8/2011 |
| HK | 1087324 | A1 | 11/2011 |
| HK | 1104776 | A1 | 11/2011 |
| JP | 2006510403 | A | 3/2006 |
| JP | 2007514470 | A | 6/2007 |
| JP | 2011519713 | A | 7/2011 |
| JP | 2011224384 | A | 11/2011 |
| JP | 2012091033 | A | 5/2012 |
| JP | 2012176318 | A | 9/2012 |
| JP | 5053515 | B2 | 10/2012 |
| JP | 2012187415 | A | 10/2012 |
| JP | 2012523897 | A | 10/2012 |
| JP | 5074036 | B2 | 11/2012 |
| JP | 2012531265 | A | 12/2012 |
| JP | 2013503007 | A | 1/2013 |
| JP | 5148284 | B2 | 2/2013 |
| JP | 5198069 | B2 | 5/2013 |
| JP | 2014000425 | A | 1/2014 |
| KR | 20050072500 | A | 7/2005 |
| KR | 20050084024 | A | 8/2005 |
| KR | 20120090997 | A | 8/2012 |
| KR | 20120102576 | A | 9/2012 |
| MX | 2012007140 | A | 1/2013 |
| NZ | 597261 | A | 11/2013 |
| SG | 173840 | A1 | 9/2011 |
| SG | 175229 | A1 | 11/2011 |
| SG | 176833 | A1 | 1/2012 |
| SG | 178836 | A1 | 4/2012 |
| SG | 193484 | A1 | 10/2013 |
| TW | 200509870 | A | 3/2005 |
| TW | 1231755 | B | 5/2005 |
| TW | 200800123 | A | 1/2008 |
| TW | 1330075 | B | 9/2010 |
| WO | 2004049981 | A3 | 6/2004 |
| WO | 2004051301 | A3 | 6/2004 |
| WO | 2005051239 | A1 | 6/2005 |
| WO | 2005051240 | A1 | 6/2005 |
| WO | 2006058057 | A2 | 6/2006 |
| WO | 2006060795 | A1 | 6/2006 |
| WO | 2006058057 | A8 | 7/2006 |
| WO | 2007041375 | A2 | 4/2007 |
| WO | 2007062103 | A1 | 5/2007 |
| WO | 2007070339 | A2 | 6/2007 |
| WO | 2007092841 | A2 | 8/2007 |
| WO | 2007109641 | A2 | 9/2007 |
| WO | 2007092841 | A3 | 11/2007 |
| WO | 2007109641 | A3 | 12/2007 |
| WO | 2008101090 | A2 | 8/2008 |
| WO | 2008112996 | A1 | 9/2008 |
| WO | 2008101090 | A3 | 11/2008 |
| WO | 2009/001083 | A1 | 12/2008 |
| WO | 2008157412 | A2 | 12/2008 |
| WO | 2007041375 | A3 | 4/2009 |
| WO | 2008157412 | A3 | 4/2009 |
| WO | 2009134672 | A1 | 5/2009 |
| WO | 2009111626 | A2 | 9/2009 |
| WO | 2009111639 | A1 | 9/2009 |
| WO | 2009111656 | A1 | 9/2009 |
| WO | 2009140294 | A1 | 11/2009 |
| WO | 2009111626 | A3 | 1/2010 |
| WO | 2010099231 | A2 | 9/2010 |
| WO | 2010099353 | A1 | 9/2010 |
| WO | 2010121147 | A1 | 10/2010 |
| WO | 2010124164 | A1 | 10/2010 |
| WO | 2010099231 | A3 | 11/2010 |
| WO | 2011028624 | A1 | 3/2011 |
| WO | 2011056995 | A2 | 5/2011 |
| WO | 2011072235 | A2 | 6/2011 |
| WO | 2011075697 | A2 | 6/2011 |
| WO | 2011056995 | A3 | 9/2011 |
| WO | 2011075697 | A3 | 10/2011 |
| WO | 2011072235 | A3 | 12/2011 |
| WO | 2012112694 | A1 | 8/2012 |
| WO | 2012112694 | A2 | 8/2012 |
| WO | 2012112698 | A2 | 8/2012 |
| WO | 2012112701 | A2 | 8/2012 |
| WO | 2012112702 | A2 | 8/2012 |
| WO | 2012112694 | A3 | 1/2013 |
| WO | 2012112701 | A3 | 1/2013 |
| WO | 2012112702 | A3 | 1/2013 |
| WO | 2013020026 | A1 | 2/2013 |
| WO | 2013025814 | A1 | 2/2013 |
| WO | 2012112698 | A3 | 3/2013 |
| WO | 2013056036 | A1 | 4/2013 |
| WO | 2013119790 | A1 | 8/2013 |
| WO | 2013119865 | A1 | 8/2013 |
| WO | 2013131066 | A1 | 9/2013 |
| WO | 2013152341 | A1 | 10/2013 |
| WO | 2013155500 | A1 | 10/2013 |
| WO | 2013155501 | A1 | 10/2013 |
| WO | 2014008444 | A1 | 1/2014 |
| WO | 2014035991 | A1 | 3/2014 |
| WO | 2014047514 | A1 | 3/2014 |

* cited by examiner

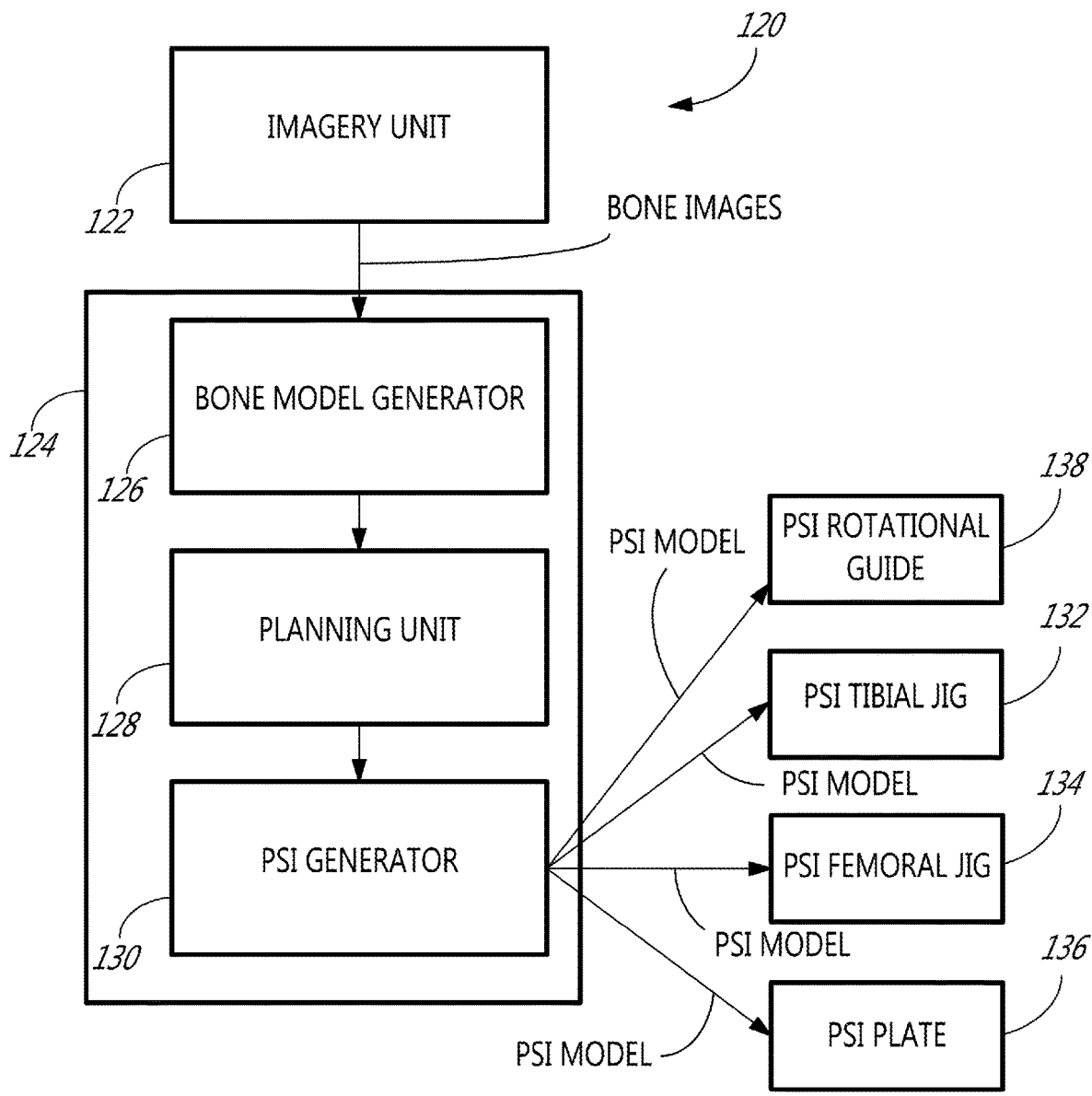

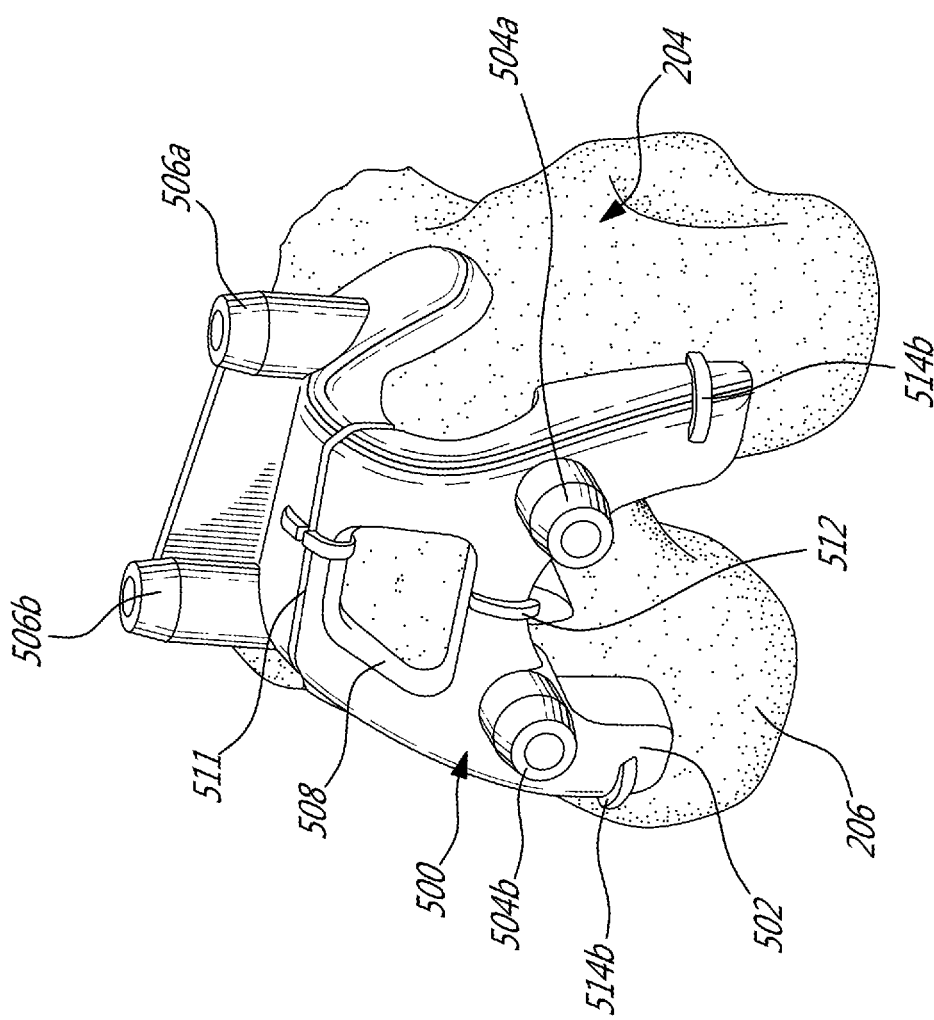
Fig_10a

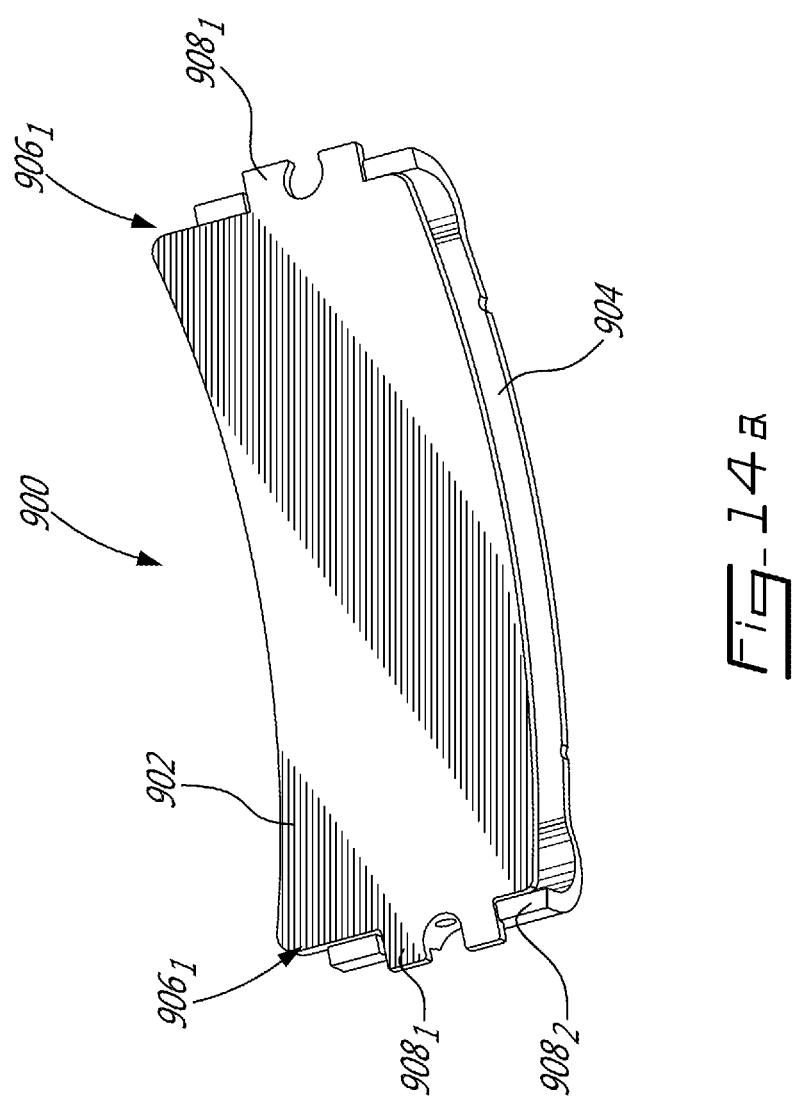

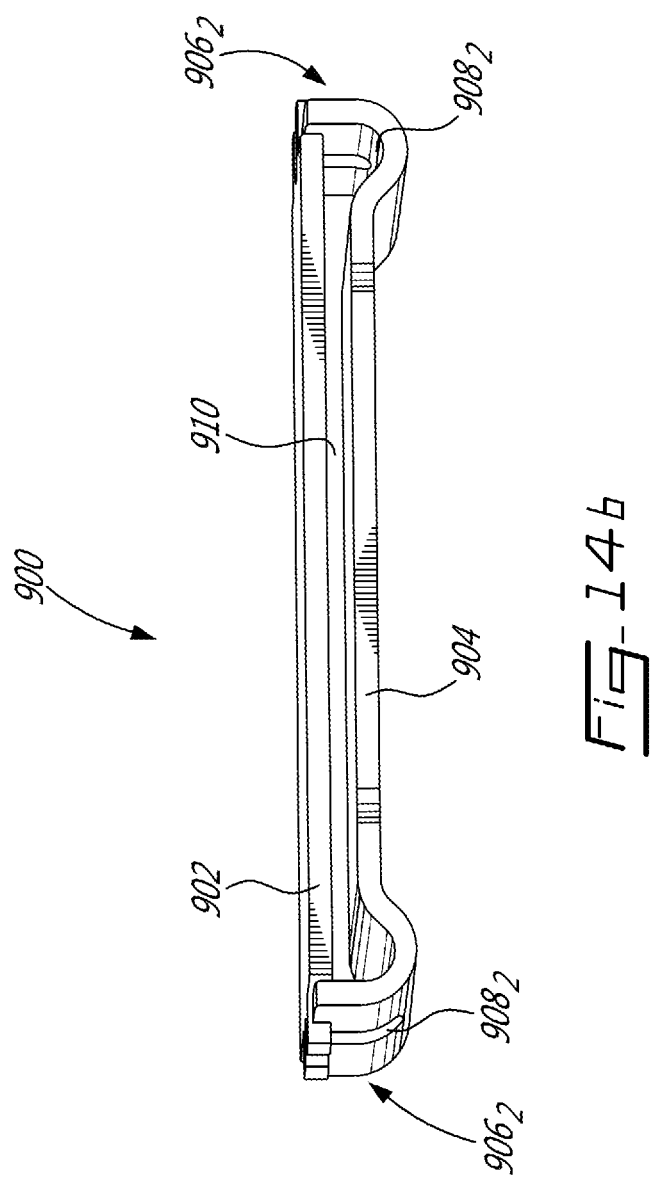

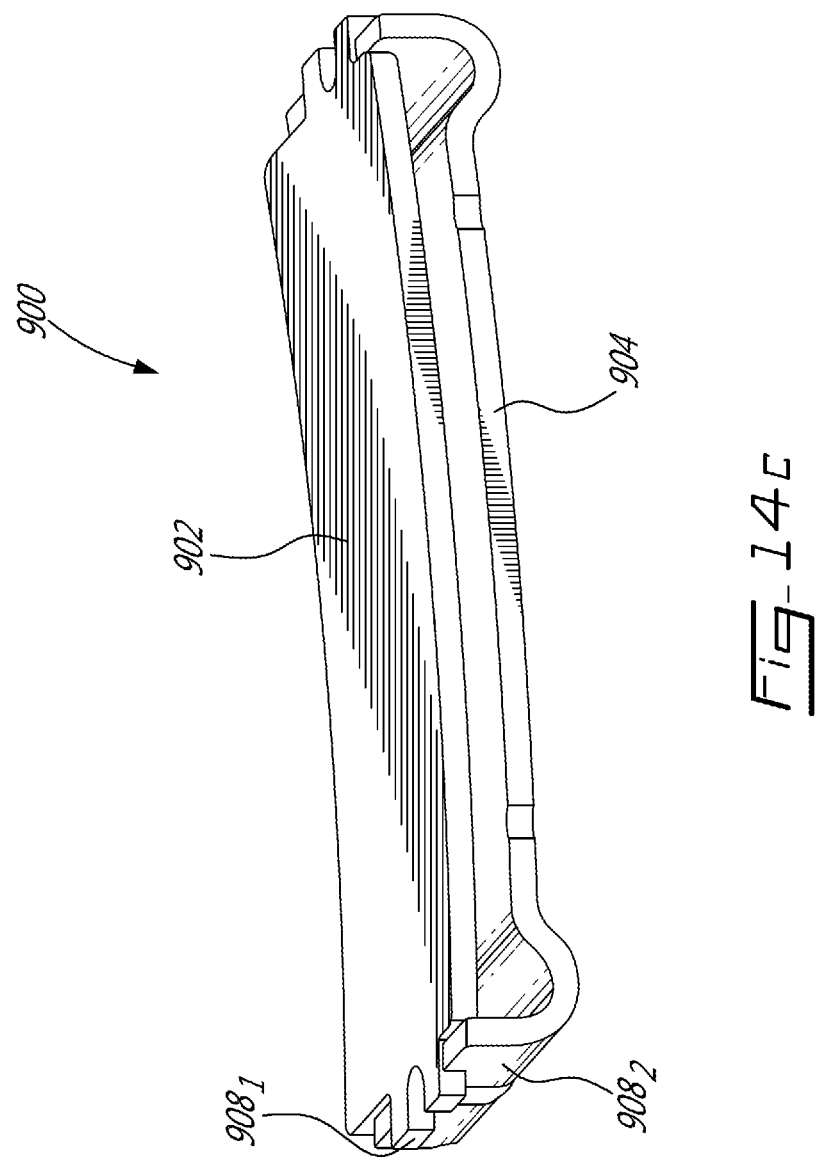
Fig_14c

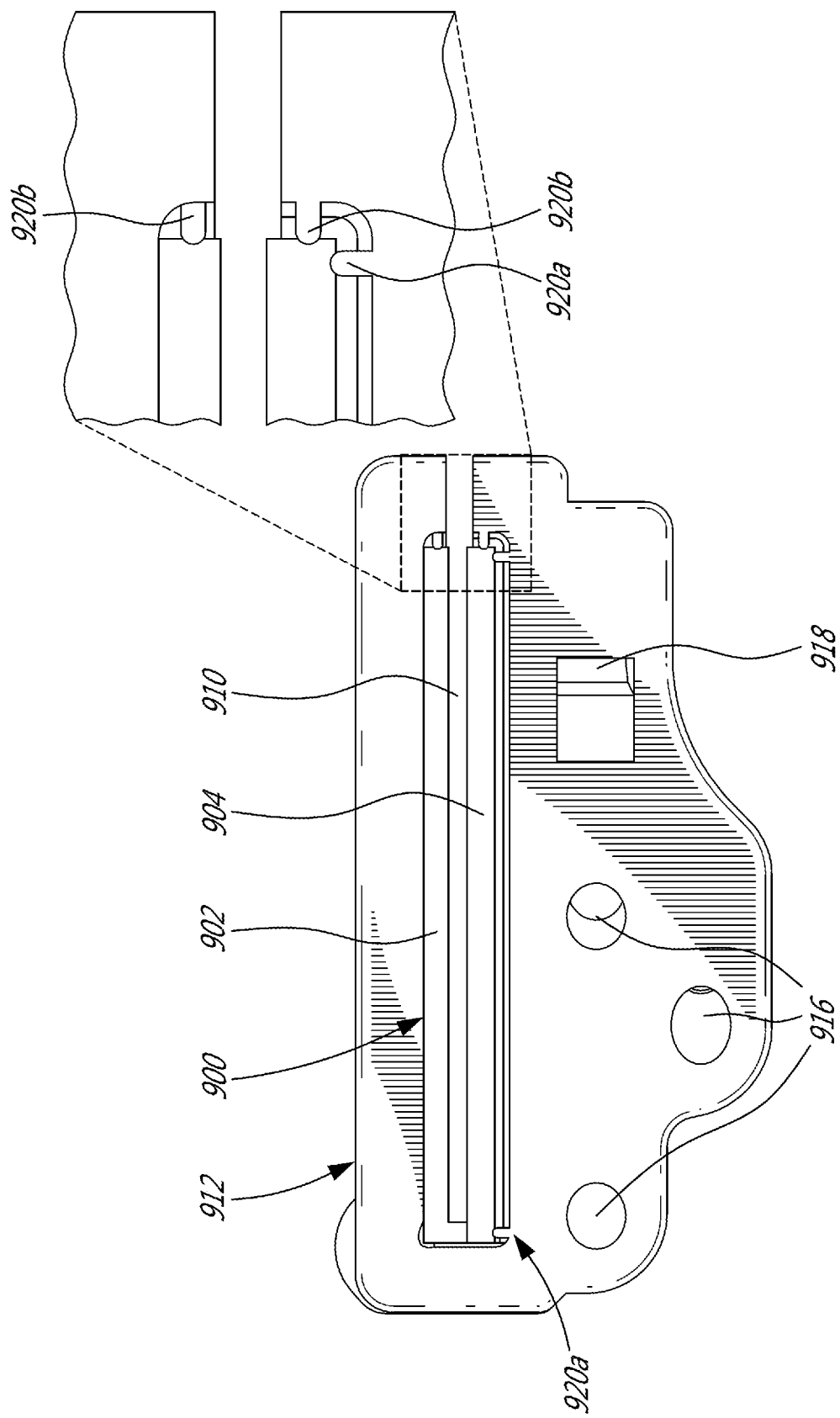

PATIENT-SPECIFIC INSTRUMENTATION AND METHOD FOR ARTICULAR JOINT REPAIR

CROSS-REFERENCE TO RELATED APPLICATION

The present application is a continuation of U.S. patent application Ser. No. 13/902,219 filed on May 24, 2013 which claims priority of U.S. provisional Application Ser. No. 61/651,061, filed on May 24, 2012, U.S. Provisional Patent Application No. 61/671,990, filed on Jul. 16, 2012, and U.S. Provisional Patent Application No. 617/87579, filed on Mar. 15, 2013.

FIELD OF THE APPLICATION

The present application relates to patient-specific instrumentation for articular joint repair.

BACKGROUND OF THE ART

In arthroplasty, a damaged joint, such as a knee joint, is replaced with prosthetic implants. Prior to implantation of the implant, the damaged region of the joint is typically prepared by treating regions of the bones to provide surfaces that can align with and therefore accommodate the implant.

Accuracy in the alignment of the implant is important in the arthroplasty procedure. In knee replacement surgery, this entails proper alignment of the knee so the centre of the hip, knee and ankle are aligned in a straight line. This in turn ensures faster patient rehabilitation and better knee function. For this purpose, mechanical jigs, which ensure accurate position and orientation of finishing instruments used during bone resection, are typically used during arthroplasty procedures, such as knee replacements. However, such conventional jigs may lack precision as they may rely on the user's judgment to assess proper positioning of the devices. In addition, each patient's anatomy being different, proper component sizing may be required for optimizing the outcome of the surgery. Still, conventional components only allow patient customization to a certain degree. As such, the use of conventional instrumentation can lead to misalignment and result in instability and potential wear or even premature failure of the prosthetic implants.

There is therefore a need for improved patient-specific instrumentation for use during articular joint repair procedures.

SUMMARY OF THE APPLICATION

It is therefore an aim of the present invention to provide novel patient-specific instrumentation and method.

Therefore, in accordance with the present application, there is provided a patient-specific rotational guide for guiding a positioning of a tool on a resected surface of a bone in an articular joint repair procedure, the rotational guide comprising a body comprising a tool attachment member adapted to be secured to the tool; and a bone contacting member having a bone contacting surface shaped using patient-specific modeling to conform to a shape of an articular surface of the bone for matingly contacting the articular surface when the tool is positioned on the resected surface.

Still further in accordance with the present application, the tool attachment member has an inner contour conforming to a shape of the tool for retaining the tool attachment member in position relative to the tool when the tool attachment member is secured to the tool.

Still further in accordance with the present application, the tool attachment member has an outer contour conforming to a perimeter of the tool.

Still further in accordance with the present application, the tool attachment member comprises at least one attachment means securing the tool attachment member to the tool.

Still further in accordance with the present application, the body comprises at least one alignment element located on the body using patient-specific modeling for guiding the positioning of the tool on the resected surface of the bone.

Still further in accordance with the present application, the at least one alignment element is indicative of at least one anatomic direction of the bone.

Still further in accordance with the present application, the at least one alignment element is indicative of at least one of a mechanical axis, a medio-lateral direction, and an anterior-posterior direction of the bone.

Still further in accordance with the present application, the tool has formed therein at least one aperture and the at least one alignment element comprises at least one opening adapted to cooperate with the at least one aperture when the tool attachment member is secured to the tool, the cooperating at least one aperture and at least one opening adapted to receive therein at least one fixation for securing the tool to the resected surface.

Further in accordance with the present application, there is provided a patient-specific jig for preparing an articular surface of a bone in an articular joint repair procedure, the patient-specific jig comprising at least one bone contacting member having a mating surface shaped using patient-specific modeling to conform to a shape of the articular surface, the mating surface adapted to matingly contact a portion of the articular surface; and a cutting guide adjacent the at least one bone contacting member and adapted to receive therein a saw blade for resecting the articular surface.

Still further in accordance with the present application, the at least one bone contacting member has formed therein at least one clearance shaped to conform to a shape of at least one selected area of the articular surface for preventing contact between the mating surface and the at least one selected area.

Still further in accordance with the present application, the at least one clearance is shaped to prevent contact between the mating surface and at least one of cartilage, soft tissue, osteophytes, and menisci.

Still further in accordance with the present application, the mating surface of the at least one bone contacting member is adapted to matingly contact a distal surface of a lateral femoral condyle, a distal surface of a medial femoral condyle, an anterior surface of the lateral femoral condyle, and an anterior surface of the medial femoral condyle.

Still further in accordance with the present application, mating surface of the at least one bone contacting member is adapted to matingly contact a proximal surface of a lateral tibial plateau, a proximal surface of a medial tibial plateau, and an anterior proximal tibial surface.

Still further in accordance with the present application, the mating surface of the at least one bone contacting member is shaped to conform to a shape of a tibial intercondylar eminence for securing a medio-lateral position and a rotation of the jig relative to the bone when the mating surface matingly contacts the articular surface.

Still further in accordance with the present application, the mating surface of the at least one bone contacting member has a first size proportional to a second size of the bone.

Still further in accordance with the present application, the at least one bone contacting member comprises at least one alignment element defined on the at least one bone contacting member using patient-specific modeling for guiding a positioning of the jig on the resected surface of the bone.

Still further in accordance with the present application, the at least one alignment element is indicative of at least one anatomical direction of the bone.

Still further in accordance with the present application, the at least one alignment element is indicative of at least one of an anterior-posterior direction of the bone and a mechanical axis of the bone.

Still further in accordance with the present application, the at least one alignment element is indicative of a plane along which the articular surface is to be resected.

Still further in accordance with the present application, the cutting guide comprises an opening for receiving therein an insert, the insert comprising a first member and a second member coupled to the first member and spaced therefrom for defining an aperture adapted to receive therein the saw blade.

Further in accordance with the present application, there is provided a cut slot for use in resecting an articular bone surface in an articular joint repair procedure, the cut slot comprising a housing adapted to be positioned adjacent the articular bone surface, the housing having an opening defined therein; and an insert adapted to be fitted into the opening, the insert having defined therein an aperture adapted to receive a saw blade for resecting the articular bone surface.

Still further in accordance with the present application, the insert comprises a first member and a second member coupled to the first member, the second member spaced from the first member for defining the aperture.

Still further in accordance with the present application, the first member and the second member each have a first end and a second end opposite the first end and are each provided with a first attachment means at the first end and with a second attachment means at the second end, the first attachment means of the first member adapted to cooperate with the first attachment means of the second member and the second attachment means of the first member adapted to cooperate with the second attachment means of the second member for coupling the first member to the second member.

Still further in accordance with the present application, the housing comprises at least one crush rib for securing a position of the insert within the opening, the at least one crush rib adapted to be resiliently deformed in response to a pressure being exerted thereon as the insert is fitted into the opening.

Still further in accordance with the present application, the housing comprises a first, a second, a third, and a fourth crush rib and further wherein, with the insert fitted into the opening, the first crush rib is positioned adjacent the first end of the first member, the second crush rib is positioned adjacent the first end of the second member, and the third and fourth crush ribs are positioned adjacent a lower surface of the second member.

Still further in accordance with the present application, the housing has formed therein at least one opening adapted to receive therein a drill bit for drilling at least one hole into the articular bone surface, the at least one hole adapted to receive at least one fixation for securing the cut slot on the articular bone surface.

Still further in accordance with the present application, the cut slot further comprises at least one bushing adapted to be received in the at least one opening, the at least one bushing configured to accommodate therein the drill bit and to prevent residual debris resulting from the drilling of the at least one hole.

Still further in accordance with the present application, the insert has a substantially constant width along a length thereof.

Still further in accordance with the present application, the first and second members are made of a stamped sheet of metal.

Still further in accordance with the present application, the housing is made of a plastic material.

Further in accordance with the present application, there is provided a patient-specific plate for preparing a resected surface of a bone to receive thereon a prosthesis component in an articular joint repair procedure, the patient-specific plate comprising a body shaped using patient-specific modeling and having a contour conforming to a perimeter of the resected surface, the body comprising a bone contacting face adapted to be positioned on the resected surface, and a prosthesis receiving face opposite the bone contacting face, the prosthesis receiving face comprising at least one alignment element defined using patient-specific modeling for guiding a positioning of the prosthesis component on the prosthesis receiving face.

Still further in accordance with the present application, the prosthesis receiving face has delineated thereon an outline of the prosthesis component.

Still further in accordance with the present application, the at least one guiding element is indicative of at least one anatomic direction of the bone for guiding the positioning of the prosthesis component relative to the at least one anatomic direction.

Still further in accordance with the present application, the at least one guiding element is indicative of at least one of a medio-lateral direction and an anterior-posterior direction of the bone.

Still further in accordance with the present application, the at least one guiding element comprises at least one aperture indicative of at least one location on the resected surface at which to drill at least one hole, the at least one hole adapted to receive therein at least one fixation for securing on the resected surface a tool for use in the articular joint repair procedure.

Further in accordance with the present application, there is provided a method for manufacturing a patient-specific jig for use in preparing an articular surface of a bone in an articular joint repair procedure, the method comprising acquiring image data of the bone; generating a three-dimensional model of the bone using the acquired image data; providing a jig blank model; and applying a Boolean operation for removing material from the jig blank model thereby deconstructing the jig blank model, a shape of the deconstructed jig blank model conforming to a shape of the three-dimensional model of the bone.

Still further in accordance with the present application, applying the Boolean operation causes the deconstructed jig blank model to have at leas one bone contacting surface conforming to the articular surface of the bone, the at least one bone contacting surface adapted to be positioned on the articular surface.

BRIEF DESCRIPTION OF THE DRAWINGS

FIG. 1b is a flow chart of the step of creating a patient-specific jig of FIG. 1a;

FIG. 2 is a block diagram of a patient-specific instrumentation computer-assisted system for arthroplasty in accordance with the present disclosure;

FIG. 10a is a bottom perspective view of a patient-specific femoral jig on a femur in accordance with an alternative embodiment of the present disclosure;

FIG. 10b is a side view of the femoral jig of FIG. 10a;

FIG. 11b is a top view of the tibial jig of FIG. 11a;

FIG. 11c is a top perspective view of the tibial jig of FIG. 11a;

FIG. 14a is a top perspective view of a cut slot in accordance with the present disclosure;

FIG. 14b is a front view of the cut slot of FIG. 14a;

FIG. 14c is a perspective view of the cut slot of FIG. 14a;

FIG. 14g is a front view of the cut slot of FIG. 14d with a close-up view of crush ribs in accordance with the present disclosure.

DESCRIPTION OF THE EXEMPLARY EMBODIMENTS

Figure 1A:
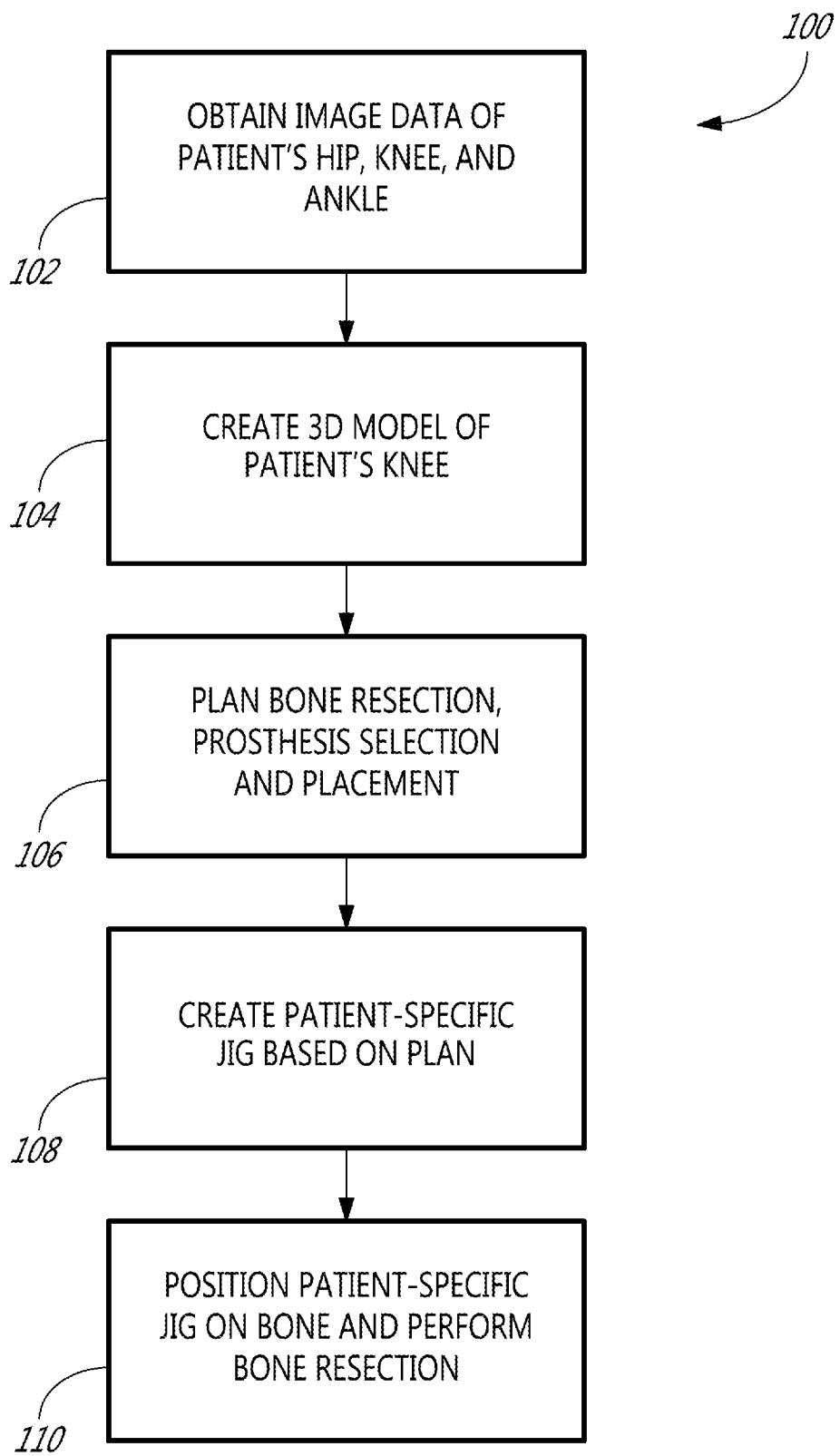
FIG. 1a is a flow chart of a method for performing bone resection during arthroplasty using a patient-specific jig in accordance with the present disclosure.

Referring to FIG. 1a, a method 100 for preparing a bone using patient-specific instrumentation (PSI), and more particularly patient-specific femoral and tibial jigs, prior to performing an arthroplasty procedure, such as knee replacement, will now be described. Although described herein as relating to total knee replacement, it should be understood that the method 100 is also suitable for partial knee replacement, or other articular joint repair procedures known to those skilled in the art. It should also be understood that the method 100 may be suitable for repairing other articular joints, such as an elbow, shoulder, wrist, or hip.

The first step 102 of the method 100 illustratively comprises pre-operative planning, during which image data of the patient's anatomy, e.g. the hip, knee, and ankle regions when total knee replacement is concerned, may be obtained before surgery. The image data may be obtained from scans generated using Magnetic Resonance Imaging (MRI), Computed Tomography (CT), ultrasound, x-ray technology, optical coherence tomography, or the like. Once the images are obtained, a computer software creates a three dimensional (3D) model of the patient's damaged knee joint (step 104), which may be sent to a user over a suitable communication network, such as the Internet. The user may then visualize the 3D model using a computer (not shown) to plan bone resection and prosthesis component placement at the damaged joint region (step 106). The model further enables the user to determine the prosthesis sizing and shape option, e.g. thickness, length, width, or curvature, best adapted to the patient given the latter's age, weight, gender, and other pertinent information.

Figure 1B:
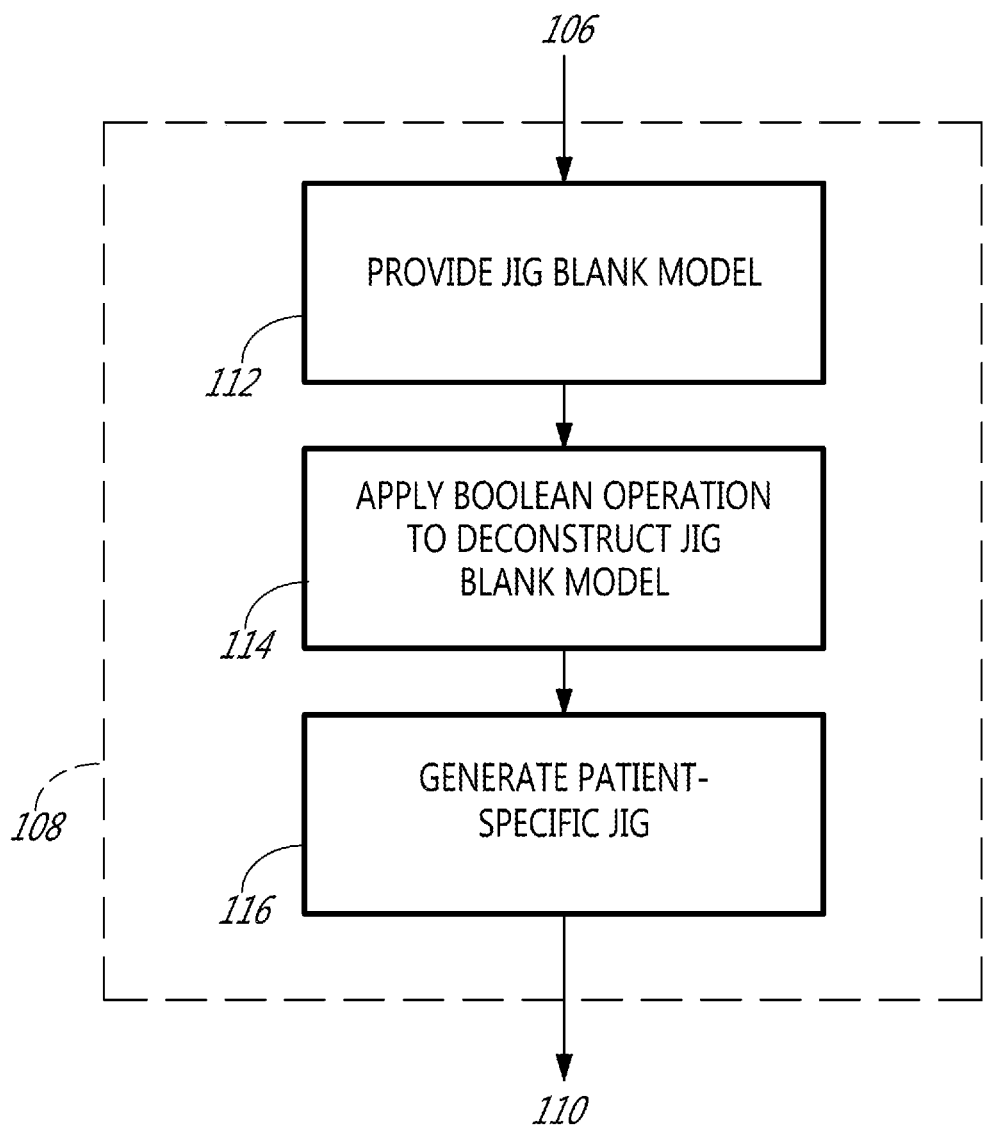

Referring to FIG. 1b in addition to FIG. 1a, once bone resection and prosthesis selection and placement have been planned by the user, the user's computer plan may be used to manufacture patient-specific jigs (step 108). The patient-specific jigs may be manufactured using a jig blank model as a starting point for the machining process (step 112). The jig blank model may be made of any suitable material, including but not limited to a polymer, a metal, a cross-linked polymer, a ceramic, and an alloy. In this case, a jig blank model of a given size, e.g. small, medium, or large, selected from a library of blanks and adapted to the anatomy of the patient's damaged joint may be deconstructed. Parts of the blank model may be removed using a Boolean operation to carve out the desired shape of the patient-specific jigs (step 114). A jig having a surface conforming to the joint surface to which the prosthesis is designed to mate, and thus precisely-fitting the patient's anatomy, may then be obtained (step 116).

A rapid prototyping manufacturing process may further be used to manufacture the patient-specific jigs. In this technique, a computer software may section the 3D representations of an object to be manufactured into a plurality of distinct two-dimensional (2D) layers. A 3D printer then fabricates a layer of material for each layer sectioned by the software. The fabricated layers together form a prototype of the desired object.

During surgery, the thus manufactured jigs may be precisely fitted over the patient's knee bones, namely the femur and tibia, at the damaged region of the knee joint for guiding the bone resection (step 110). In this manner, customized bone preparation may be performed as previously planned on the computer by the user. Optimal placement of the best fitting size and shape of the replacement prosthesis may therefore be achieved.

Referring to FIG. 2, a PSI computer-assisted system for arthroplasty is generally shown at 120. The system 120 illustratively receives at an imagery unit 122 images of the patient's hip, knee, and ankle regions from any appropriate imaging technology, such as MRI or CT. The imaging technology apparatus (not shown) may be part of the system 120. The bone images are then sent to a processor unit 124, which illustratively comprises a bone model generator 126, a planning unit 128, and a PSI generator 130. The processor unit 124 has a processor to run an application that will generate PSI models used to manufacture PSI, such as a PSI tibial jig 132, a PSI femoral jig 134, a PSI plate 136, and a PSI rotational guide 138 for use during the arthroplasty procedure, as will be discussed further below. The processor unit 124 may be any appropriate computer or processing unit. User interfaces, such as a monitor, screen, touchscreen, keyboard, or mouse, may be part of the processor unit 124 for the involvement of an operator in the creation of the PSI models.

The bone model generator 126 is illustratively used to interpret the bone images received from the imagery unit 122 in order to create a 3D model of the patient's damaged articular joint, e.g. the knee joint. For this purpose, input may be provided by an operator via the user interfaces to ensure proper adequate segmentation between bone and tissue as well as bone and cartilage, thus increasing the accuracy of the generated bone model.

The planning unit 128 may then be used to visualize the bone model and to plan bone resection as well as prosthesis component placement at the damaged joint. The prosthesis size and shape best-suited to the patient's unique anatomy may also be determined at the planning unit 128. According to the generated bone model and pre-operative planning, the PSI generator 130 may produce the PSI models, which in turn may be used to manufacture at least one of the PSI tibial jig 132, the PSI femoral jig 134, the PSI plate 136, and the PSI rotational guide 138, the latter being adapted to be placed over a resected bone portion for guiding the position or rotation of a prosthesis component thereon. For this purpose, patient-specific modeling may be used to design PSI tools, e.g. the PSI tibial jig 132, the PSI femoral jig 134, the PSI plate 136, and the PSI rotational guide 138, such that each PSI tool has a mating surface that is a replica of or otherwise precisely conforms to a surface of a bone the tool is to be positioned on. In this manner, the PSI tool matingly contacts the bone surface and precisely fits the patient's anatomy. The PSI models may be in any appropriate format to allow the manufacture of PSI. For instance, the PSI models may be formatted into numerical control (NC) machine files, technical data, visual or digital models, etc.

Figure 3:
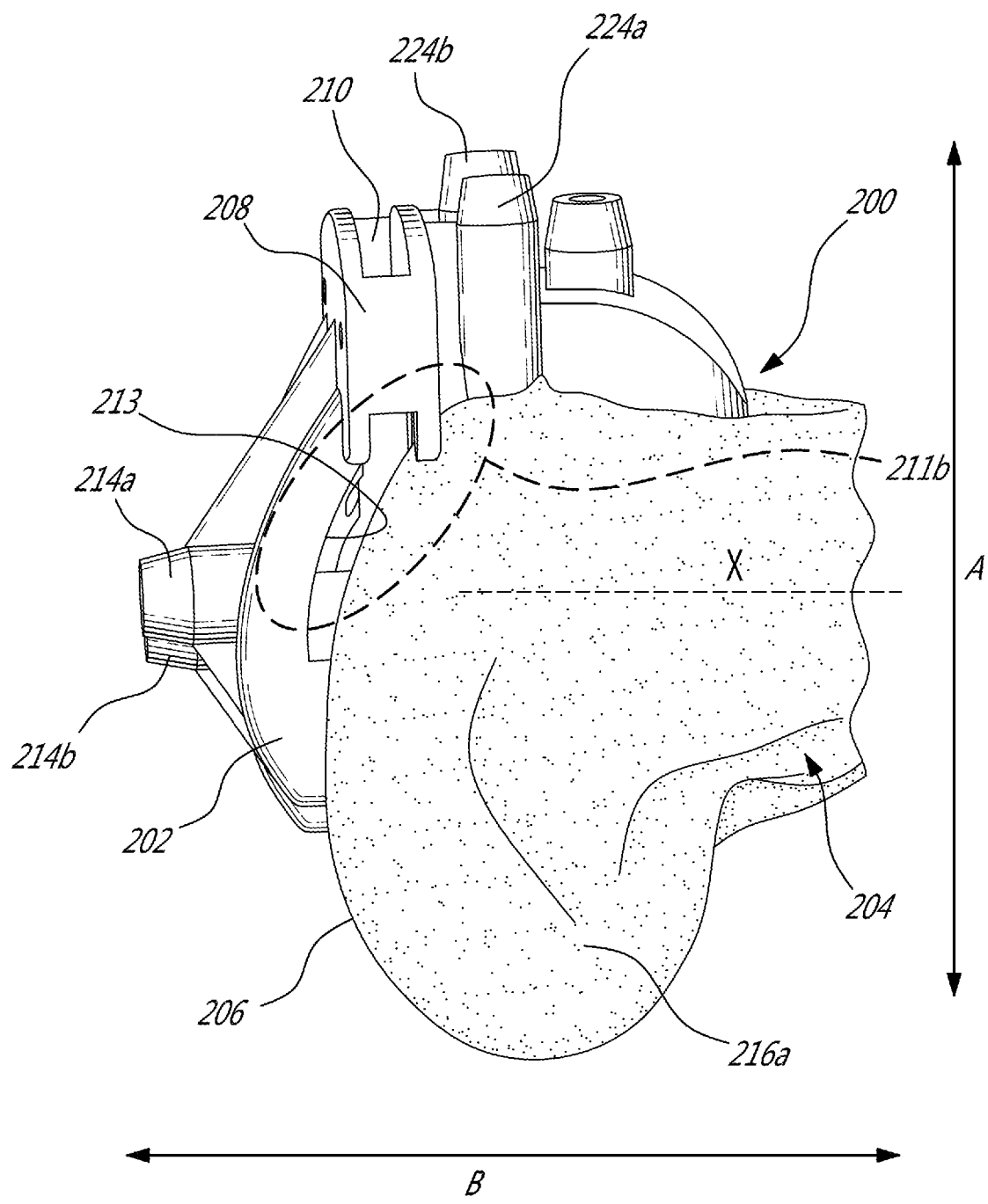
FIG. 3 is a side perspective view of a patient-specific femoral jig on a femur in accordance with the present disclosure.
Figure 4:
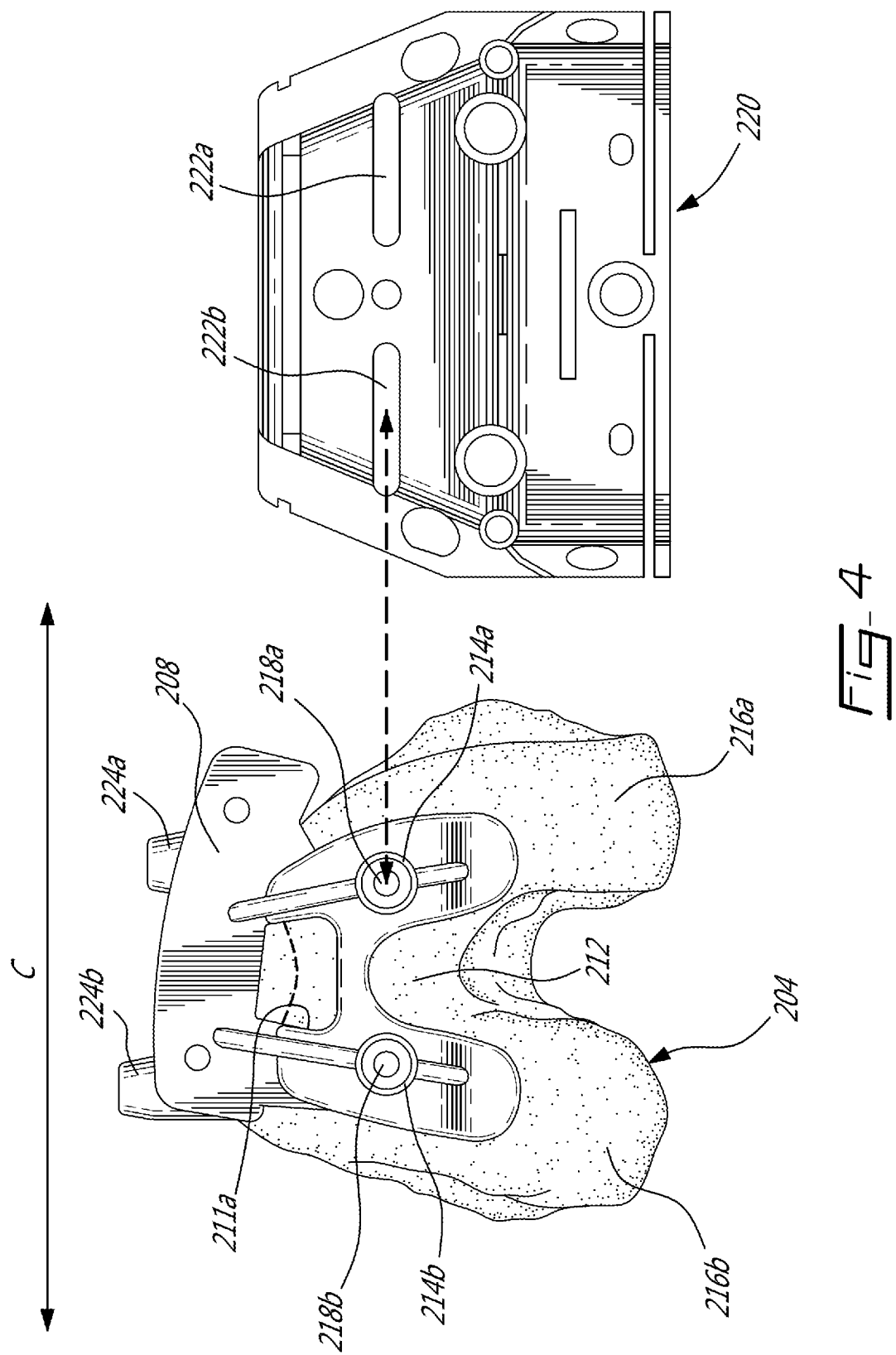
FIG. 4 is a bottom perspective view of the patient-specific femoral jig on the femur of FIG. 2.

Referring now to FIG. 3 and FIG. 4, a femoral jig 200 may first be used to prepare a distal femoral surface prior to attaching a prosthesis component thereon, in most cases with a bone cement. The femoral jig 200 illustratively comprises a bone contacting portion 202 adapted to be positioned on the patient's femur 204 in flush contact with an articular surface 206 thereof.

The femoral jig 200 illustratively comprises a cut-slot portion 208 having a cutting slot 210 formed therein and adapted to receive a saw blade (not shown) used to execute the pre-planned bone cuts. When the femoral jig 200 is in position over the femur 204 following exposure of a distal end thereof during surgery, the cut-slot portion 208 illustratively extends along the anterior-posterior direction A. In this manner, when the femoral jig 200 is in place, the slot 210 is positioned adjacent to the trochlear groove 212 at a lower portion of the femur 204, which typically mates with an upper portion of the patient's tibia (not shown) at the knee joint. The saw blade may therefore be used to resect the lower portion of the femur 204.

The bone contacting portion 202 of the femoral jig 200 further comprises a first pair of pegs 214a and 214b, which are respectively positioned adjacent to the medial and lateral femoral condyles 216a and 216b and extend away from the femur 204 along the cranial-caudal direction B when the femoral jig 200 is in place. The pegs 214a and 214b each have elongated guide bores 218a and 218b running therethrough and adapted to receive therein the drill bit of a surgical drill (not shown). In this manner, the user may drill elongated holes (not shown) into the femur 204. The thus machined holes are adapted to receive therein fixations, such as pins, screws, or the like, to couple the femoral jig 200 to the femur 204 prior to resection thereof. Proper alignment of the pegs 214a and 214b along the medio-lateral direction C may further be verified using a device, such as a cut guide 220. For this purpose, the cut guide 220 may be positioned adjacent the pegs 214a and 214b and proper alignment with features, as in 222a, 222b provided on the cut guide 220, may be verified. In particular, the bores 218a and 218b may be used as guides to drill holes in the distal end of the femur 204 for positioning the cut guide 220 in a pre-planned position. Any cuts required to position the prosthesis component in the preplanned position may be subsequently performed.

The bone contacting portion 202 of the femoral jig 200 further illustratively comprises a second pair of pegs 224a and 224b, which are positioned adjacent the cut-slot portion 208 and extend away from the femur 204 along the anterior-posterior direction A when the femoral jig 200 is in place. The pegs 224a and 224b each have elongated guide bores (not shown) running therethrough and adapted to receive therein fixations, such as pins, screws, or the like, to further securely attach the femoral jig 200 to the femur 204 prior to resection thereof. Fixations are illustratively first inserted into the pegs 224a and 224b for attaching the femoral jig 200 to the femur 204, followed by insertion of fixations into the pegs 214a and 214b for further stabilizing the femoral jig 200 in place.

Once the femoral jig 200 has been secured and stabilized, the fixations inserted into the pegs 214a and 214b may be removed to enable resection of the distal end of the femur 204. After the femur 204 has been resected, fixations may be inserted back into the pegs 214a and 214b for attaching a standard cutting block (not shown) to the resected bone. In this manner, additional cuts, e.g. remaining ones of the five femoral cuts to be performed during total knee arthroplasty, may be effected on the femur 204.

Figure 5:
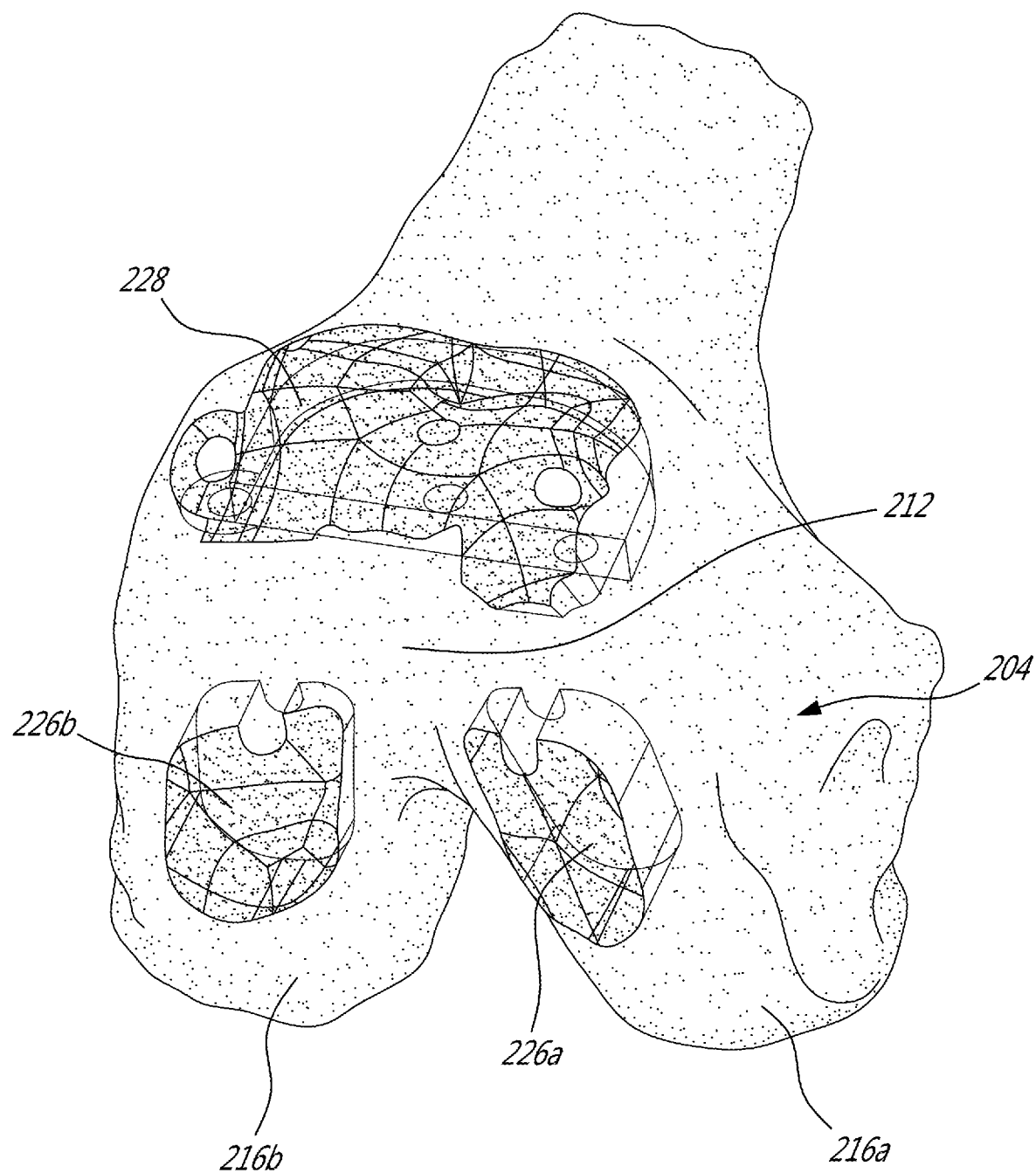
FIG. 5 is a perspective view of a femur showing femoral jig contacting areas in accordance with the present disclosure.

As can be seen from FIG. 3 and FIG. 5, the use of the femoral jig 200 advantageously enables the user to have an improved lateral view of the femur 204, in addition to having a clear view of the trochlear groove 212. Indeed, a distal clearance (reference 211a in FIG. 4) is illustratively formed in the bone contacting portion 202 in the area between the cut-slot portion 208 and the pegs 214a and 214b. The clearance 211a may be shaped and sized to conform to a shape and size of the trochlear groove 212. A lower surface 213 of the bone contacting portion 202 may also be shaped so as to contact a reduced surface of the femur 204. In particular, the shape of the lower surface 213 illustratively defines a medial clearance 211b and a lateral clearance (not shown). The medial clearance 211b and the lateral clearance provide viewing spaces that enable a user to evaluate the degree of contact between the femoral jig 200 and the distal surface of the medial and lateral femoral condyles 216a and 216b. The distal clearance 211a similarly enables to evaluate contact over the surface on the anterior part (not shown) of the condyles 216a and 216b. As seen in FIG. 5, when the femoral jig 200 is in position, the bone contacting portion 202 illustratively makes contact with the femur 204 at a medial femoral condyle contact area 226a, a lateral femoral condyle contact area 226b, and an anterior surface contact area 228. The femoral condyle contact areas 226a and 226b are illustratively positioned on the distal part of the medial and lateral femoral condyles 216a and 216b, respectively, while the anterior surface contact area 228 is positioned on the anterior part of the condyles 216a and 216b. In one embodiment, the anterior surface contact area 228 is defined by tabs (not shown) provided on the femoral jig 200 and extending over the flank of the lateral femoral condyle 216b and over the medial side (not shown) of the femur 204 accessible during the surgical procedure. The contact areas 226a, 226b, and 228 are illustratively sized so as to be proportional to the size of the femur 204. Visibility of the trochlear groove 212 further ensures that the femoral jig 200 is properly positioned on the femur 204.

The areas of contact between the femoral jig 200 and the femur 204 may vary from one patient to the next and are illustratively proportional to bone size. Still, the femoral jig 200 is illustratively designed such that, when the femoral jig 200 is in place, no contact is made with areas of the femur 204 where cartilage or soft tissues and osteophyte formation resulting from osteoarthritis may be present. For instance, in the embodiment illustrated in FIG. 5, the contact areas 226a and 226b are located on the articular surface of the femur 204 and avoid the medial and lateral margins (not shown) where osteophytes may be present. This in turn optimizes the precision of the arthroplasty procedure and improves an outcome thereof. Indeed, it is desirable for the femoral jig 200 to make contact with as few areas of the exposed femur 204 as possible so as to reduce the inaccuracies in the surgical cuts to be effected.

Figure 6:
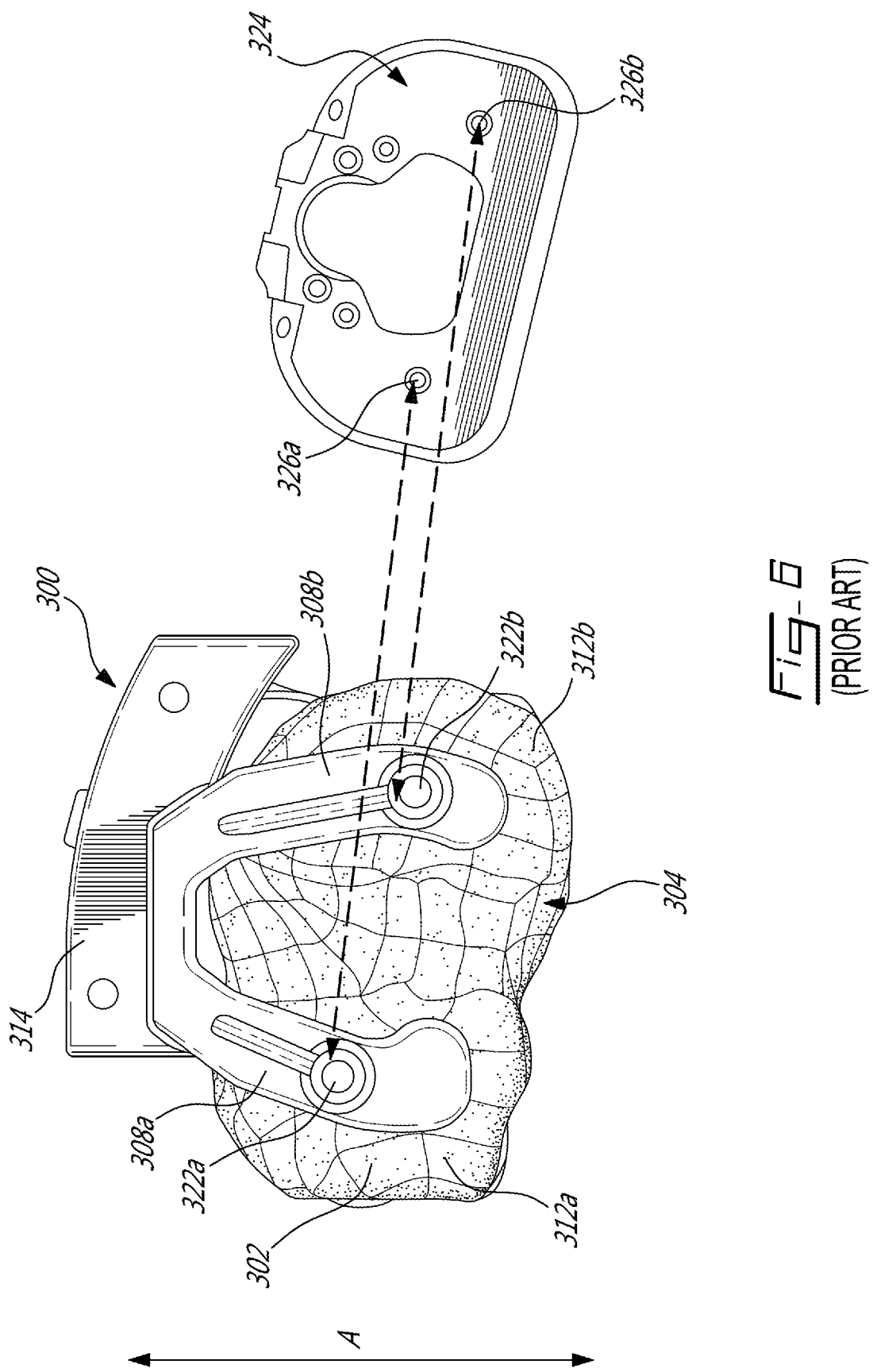
FIG. 6 is a top perspective view of a tibial jig in accordance with the prior art.
Figure 7:
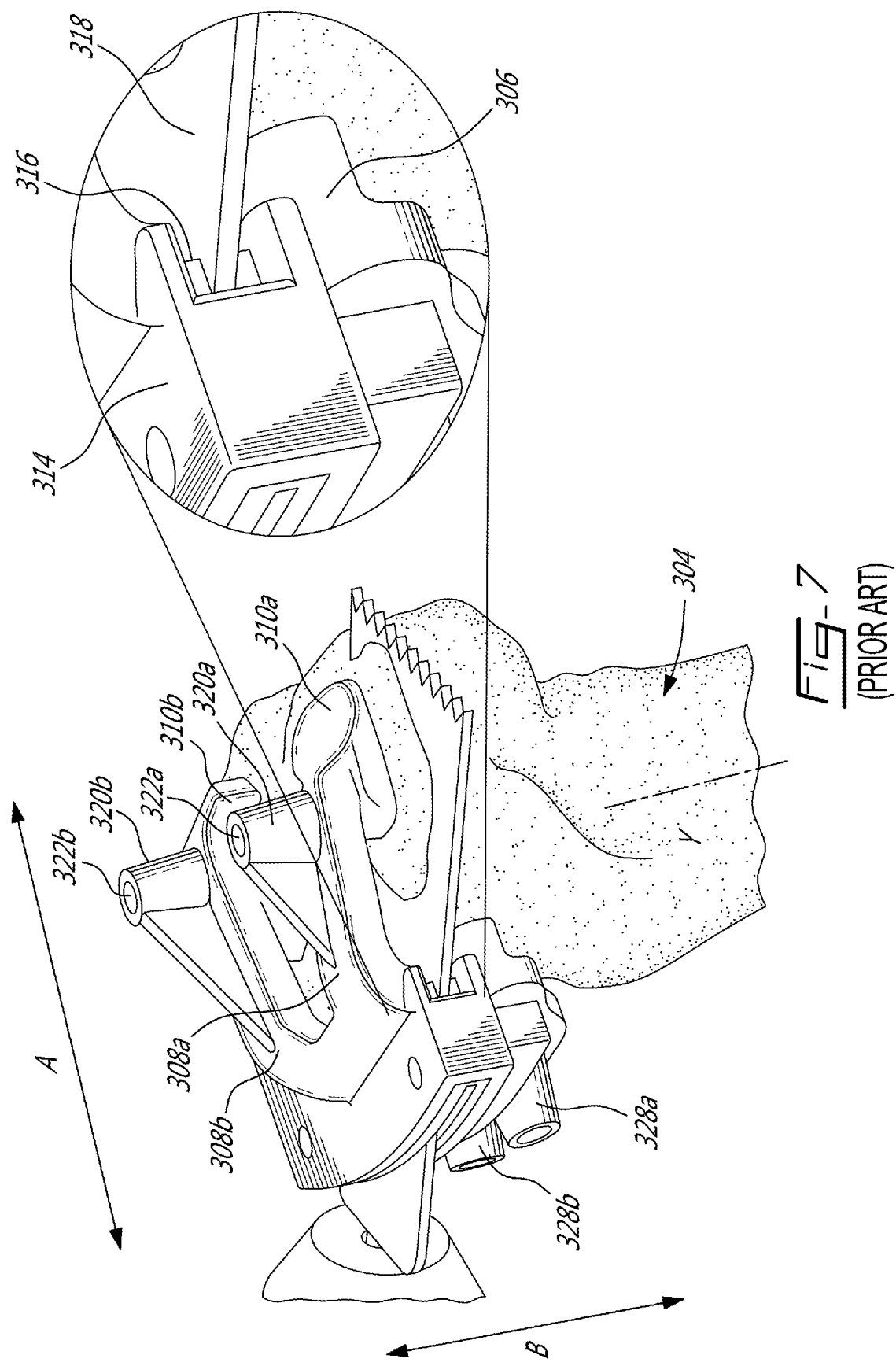
FIG. 7 is a perspective view of the tibial jig of FIG. 5.

Referring now to FIG. 6 and FIG. 7, a prior art tibial jig 300 will now be described. The tibial jig 300 is adapted to be precisely fit on an articular surface 302 of the patient's tibia 304. The tibial jig 300 illustratively comprises a tibia contacting portion 306 and a pair of attachment arms 308a and 308b each having respectively formed at an end portion thereof plateau contacting portions 310a and 310b. When the tibial jig 300 is placed over the tibia 304 following exposure of a proximal end thereof, the tibia contacting portion 306 is adapted to contact the tibia 304. The attachment arms 308a and 308b then extend away from the tibia 304 along the anterior-posterior direction A with the plateau contacting portion 310a making contact with the articular surface of the medial tibial plateau 312a and the plateau contacting portion 310b making contact with the articular surface of the lateral tibial plateau 312b.

The tibial jig 300 further comprises a cut-slot portion 314 having a slot 316 adapted to receive therein a saw blade 318 used by the user to execute the pre-planned bone cuts. When the tibial jig 300 is in place on the tibia 304, the cut-slot portion 314 is positioned adjacent an upper portion of the tibia 304, which typically mates with a lower portion of the femur 204 at the knee joint. In this position, the slot 316 extends along the transverse plane and the saw blade 318 may be inserted through the slot 316 to resect the upper portion of the tibia 304. The resected surface of the tibia 304 is in most cases perpendicular to the shaft axis Y of the tibia 304 in the coronal plane. The slot 316 may further be machined into the cut-slot portion 314 so as to enable proper reach of the saw blade 318 during the bone resection.

The pair of attachment arms 308a and 308b may respectively comprise pegs 320a and 320b, which extend away from the tibia 304 along the cranial-caudal direction B. The pegs 320a and 320b each have elongated guide bores 322a and 322b running therethrough and adapted to receive therein a surgical drill bit (not shown) used to drill elongated holes into the tibia 304. The thus machined holes are then mated with holes provided in a provisional tibial sizing plate 324 used to determine the proper size of a prosthetic tibial tray (not shown). The holes in the sizing plate 324 are adapted to receive therein fixations, such as pins, screws, or the like, to securely attach the sizing plate 324 to the resected portion of the tibia 304. For this purpose, the elongated guide bores 322a and 322b are spaced and sized to match the spacing and size of bores 326a and 326b machined into the sizing plate 324. The bores 322a and 322b thus aid in setting the position and rotation of the sizing plate 324 on the resected portion of the tibia 304. With the proper sizing plate 324 selected and held in place, the proximal tibia can be further drilled and/or broached to accommodate supporting components, such as stems, of the prosthetic tibial tray.

A second pair of pegs 328a and 328b illustratively project from the tibia contacting portion 306 and extend away from the tibia 304 along the anterior-posterior direction A when the tibial jig 300 is in place. The pegs 328a and 328b each have elongated guide bores (not shown) running therethrough and adapted to receive therein a device, such as a drop rod (not shown), for confirming, subsequent to the tibial cut, that proper rotation and alignment of the cut relative to the overall tibial shaft axis Y have been achieved using devices, such as traditional tibial component sizing jigs and rotational jigs.

Figure 8:
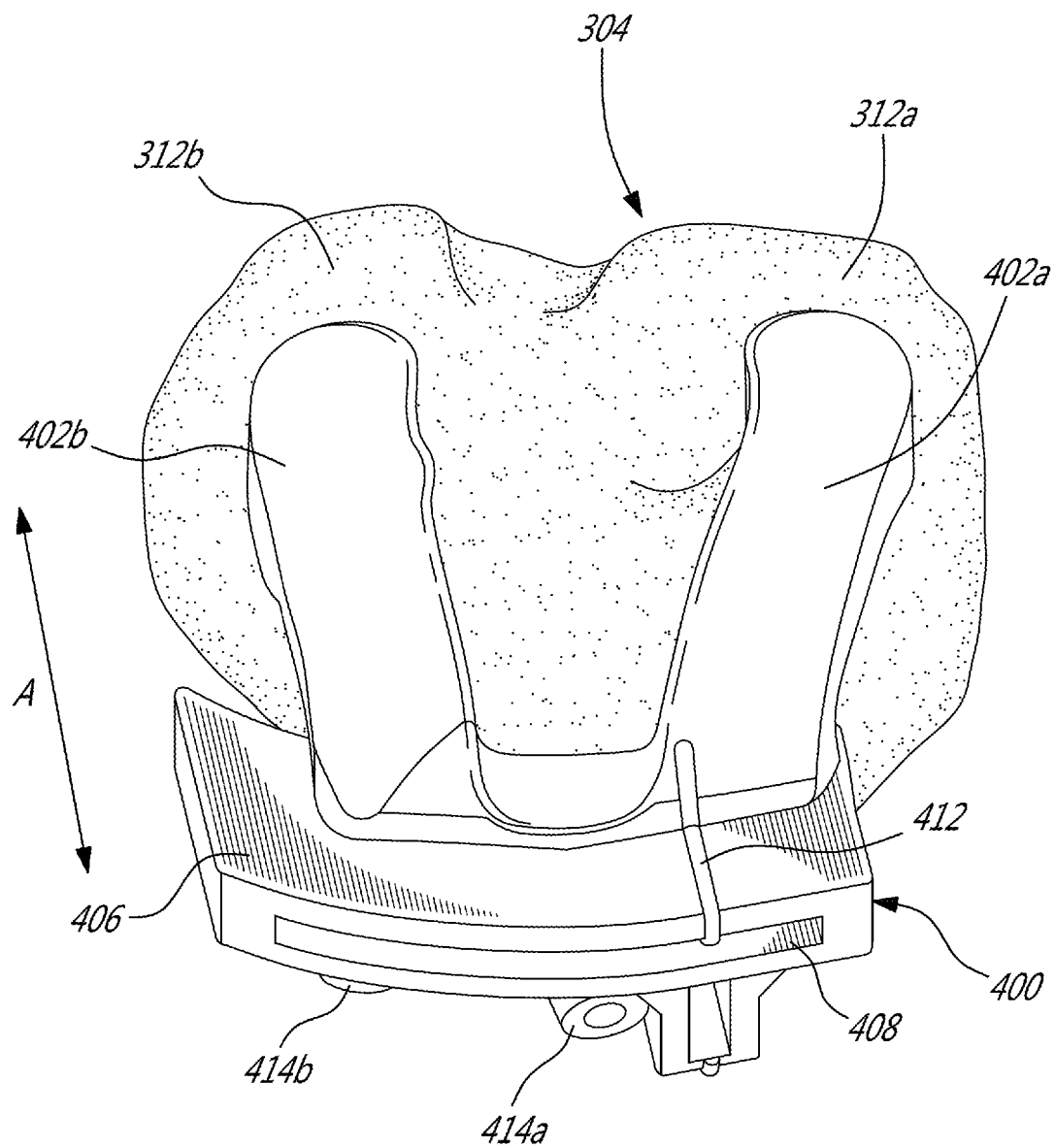
FIG. 8 is a top perspective view of a patient-specific tibial jig on a tibia in accordance with the present disclosure.
Figure 9:
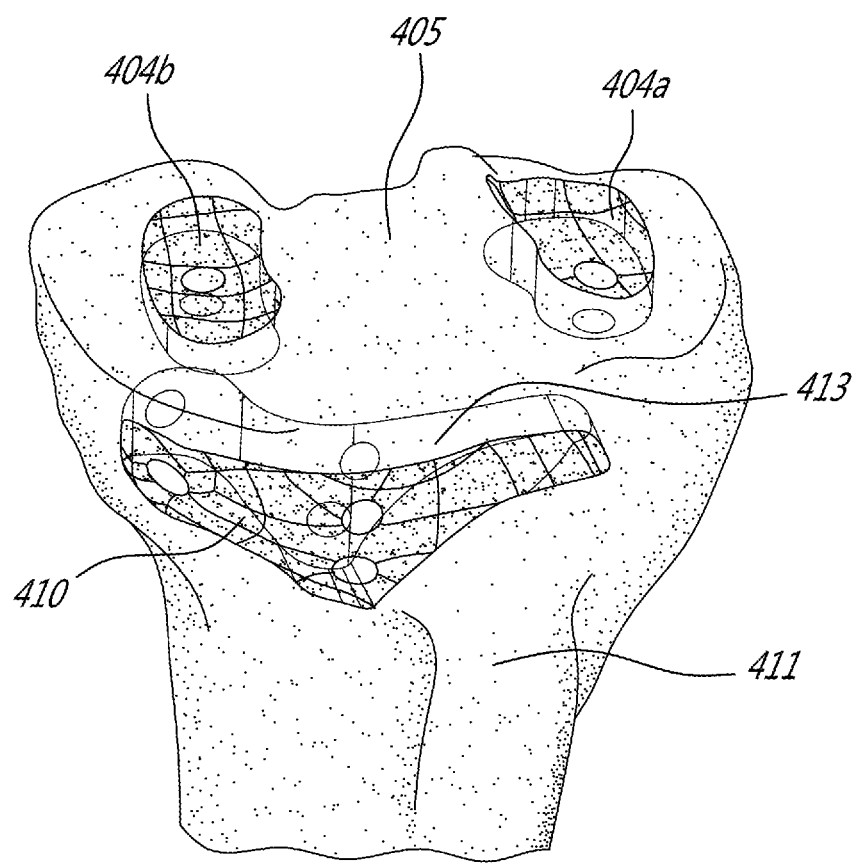
FIG. 9 is a front perspective view of a tibia showing tibial jig contacting areas in accordance with the present disclosure.

Referring to FIG. 8 and FIG. 9, a tibial jig 400 in accordance with an illustrative embodiment will now be described. The tibial jig 400 illustratively comprises a pair of attachment arms 402a and 402b each having a surface contacting portion (not shown) so that the arms 402a, 402b may respectively make contact with the articular surfaces 404a and 404b of the medial tibial plateau 312a and of the lateral tibial plateau 312b. The slope of the tibial intercondylar eminence 405 may further be used to lock the medio-lateral position as well as the rotation of the tibial jig 400. In particular, when the tibial jig 400 is in place, the attachment arms 402a and 402b may contact the sides of the intercondular eminence 405, thereby providing stability to the tibial jig 400.

The tibial jig 400 further comprises a cut-slot portion 406 having a slot 408 adapted to receive therein a saw blade (not shown) used to perform resection of the tibia 304. A tibia contacting portion (not shown) is further provided adjacent the cut-slot portion 406 for making contact with the tibia 304 on a region 410 of the medial and lateral tibial plateaus 312a and 312b adjacent the tibial tuberosity 411. When the tibial jig 400 is in position on the tibia 304, the cut-slot portion 406 is illustratively adjacent an upper portion of the tibia 304 with the slot 400 being parallel to the transverse plane. At least one line indicator 412 may further be provided on the cut-slot portion 406 adjacent the attachment arm 402a. The line indicator 412 may be locate on the jig 400 using patient-specific modeling. Alignment of the indicator 412 with the tibial tuberosity 411 may be used to confirm that the tibial jig 400 is positioned at a desired rotational angle relative to the tibia 304. In one embodiment, a first and second indicator as in 412 may be respectively provided on the anterior and distal sides cut-slot portion 406 to indicate alignment with the anterior-posterior direction A. A cut slot plane indicator (not shown) may also be provided on the medial side of the cut-slot portion 406 to indicate alignment with the plane along which the pre-planned bone cuts are to be performed.

Although the areas of contact between the tibial jig 400 and the tibia 304 may vary from one patient to the next, a lower surface (not shown) of the attachment arms 402a and 402b is illustratively sized and/or shaped such that no mating of the tibial jig 400 is made on an area 413 of the tibia 304 where meniscus may be present, thus avoiding any soft tissues remaining on the tibia 304 following exposure thereof. For instance, the arms 402a, 402b may be provided with varus-valgus shapes. Also, the tibia contacting portion is illustratively sized and/or shaped so as to avoid possible osteophytes that may be present on the anterior proximal ridge (not shown) of the tibia 304.

The tibia contacting portion illustratively has formed therein a pair of pegs 414a and 414b, which project away from the tibia contacting portion along the anterior-posterior direction A when the tibial jig 400 is in place. Elongated guide bores (not shown) may be machined into the pegs 414a and 414b for receiving fixations used to secure the tibial jig 400 to the tibia 304. If, subsequent to resection of the tibia 304 using the saw blade, it is determined that an insufficient amount of bone has been resected, a standard cutting block (not shown) may be secured to the pegs 414a and 414b for performing additional bone cuts. A clearance (not shown) having a shape and size conforming to the shape and size of the area 413 may further be formed in the tibia contacting portion to ensure that no contact is made with the area 413 of the tibia 304.

Figure 10B:
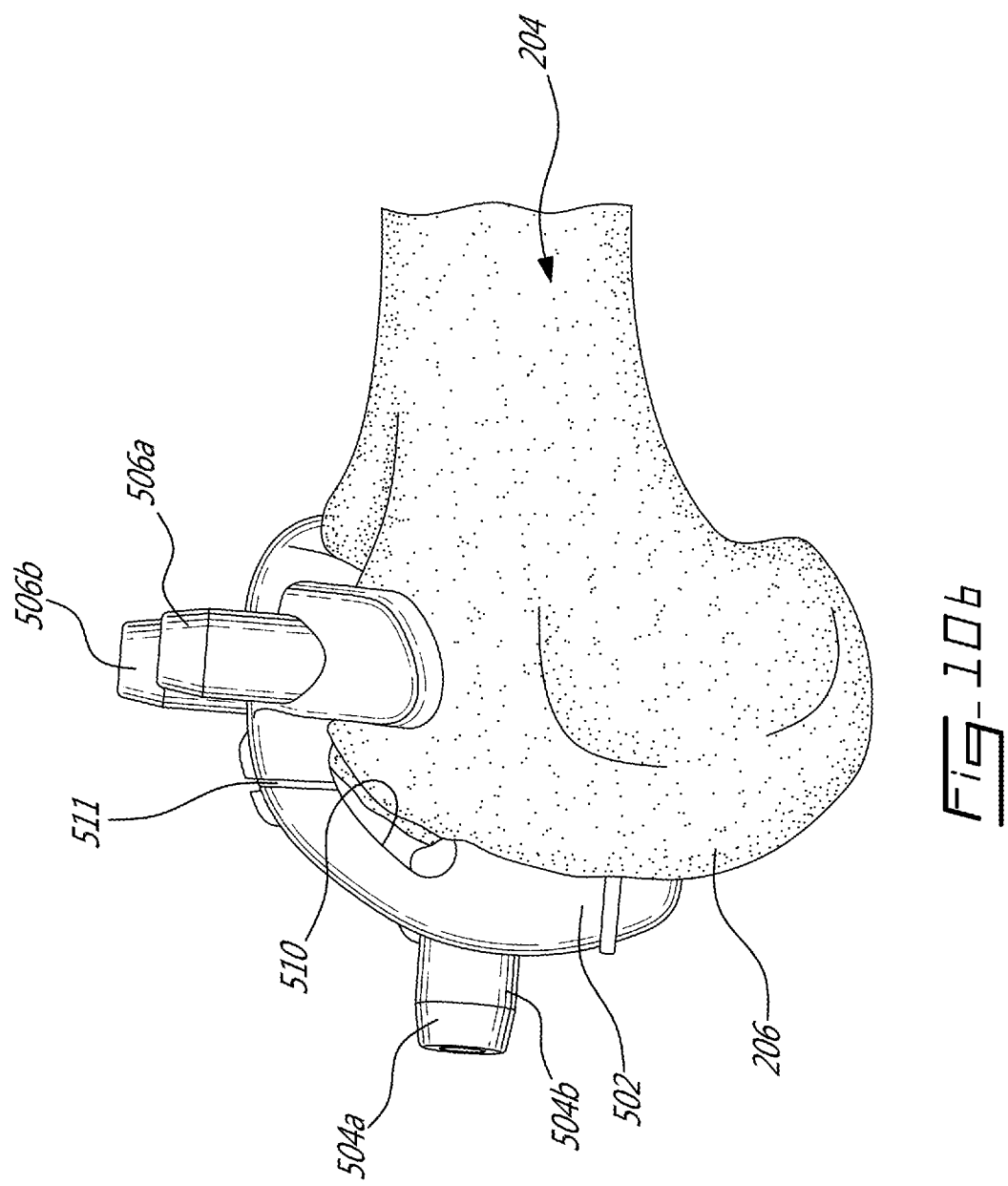

FIGS. 10a to 10b and FIGS. 11a to 11c illustrate alternate embodiments of the femoral jig 200 and of the tibial jig 400. FIG. 10a and FIG. 10b illustrate an alternate embodiment 500 of the femoral jig 200 shown in FIGS. 3 and 4. In this embodiment, the femoral jig 500 comprises a bone contacting portion 502 adapted to be positioned on the patient's femur 204 in flush contact with an articular surface 206 thereof, as produced by patient-specific fabrication. The bone contacting portion 502 further comprises a first pair of pegs 504a and 504b, which are respectively positioned adjacent to the medial and lateral femoral condyles (not shown) and extend away from the femur 204 along the cranial-caudal direction (reference B in FIG. 3) when the femoral jig 500 is in place. The pegs 504a and 504b each have elongated guide bores (not shown) running therethrough and adapted to receive therein the drill bit of a surgical drill (not shown).

The bone contacting portion 502 also comprises a second pair of pegs 506a and 506b, which extend away from the femur 204 along the anterior-posterior direction (reference A in FIG. 3) when the femoral jig 500 is in place. The pegs 506a and 506b each have elongated guide bores (not shown) running therethrough and adapted to receive therein fixations, such as pins, screws, or the like, to further securely attach the femoral jig 500 to the femur 204 prior to resection thereof.

A clearance 508 may be formed in the bone contacting portion 502 in an area between the pegs 506a and 506b and the pegs 504a and 504b. A lower surface 510 of the bone contacting portion 502 may also be shaped so as to contact a reduced surface of the femur 204.

The femoral jig 500 further comprises a line indicator 511 used to indicate the desired location of the bone cut to be performed on the femur 204. The femoral jig 500 may further comprise a mechanical axis pointer 512 provided in between the pegs 504a and 504b. The pointer 512 illustratively provides an indication as to whether the femoral jig 500 is properly positioned on the femur 204. In particular, proper positioning is achieved if the pointer 512 points towards the femur's mechanical axis (not shown), as defined during the pre-operative planning phase. A pair of transepicondylar line indicators 514a and 514b may further be provided on the bone contacting portion 502 adjacent the pegs 504a and 504b, respectively. The indicators 514a and 514b illustratively protrude away from the bone contacting portion 502 to align with the lateral and medial epicondyles (not shown).

Figure 11A:
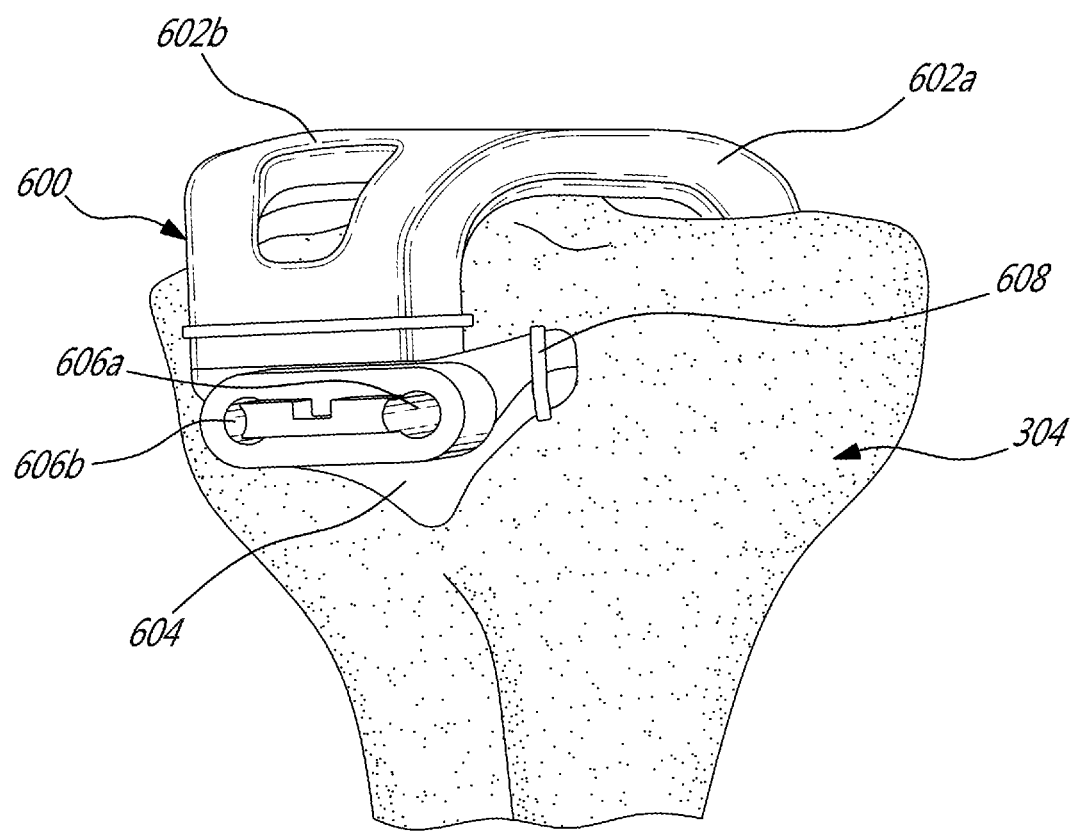
FIG. 11a is a rear perspective view of a patient-specific tibial jig on a tibia in accordance with an alternative embodiment of the present disclosure
Figure 11B:
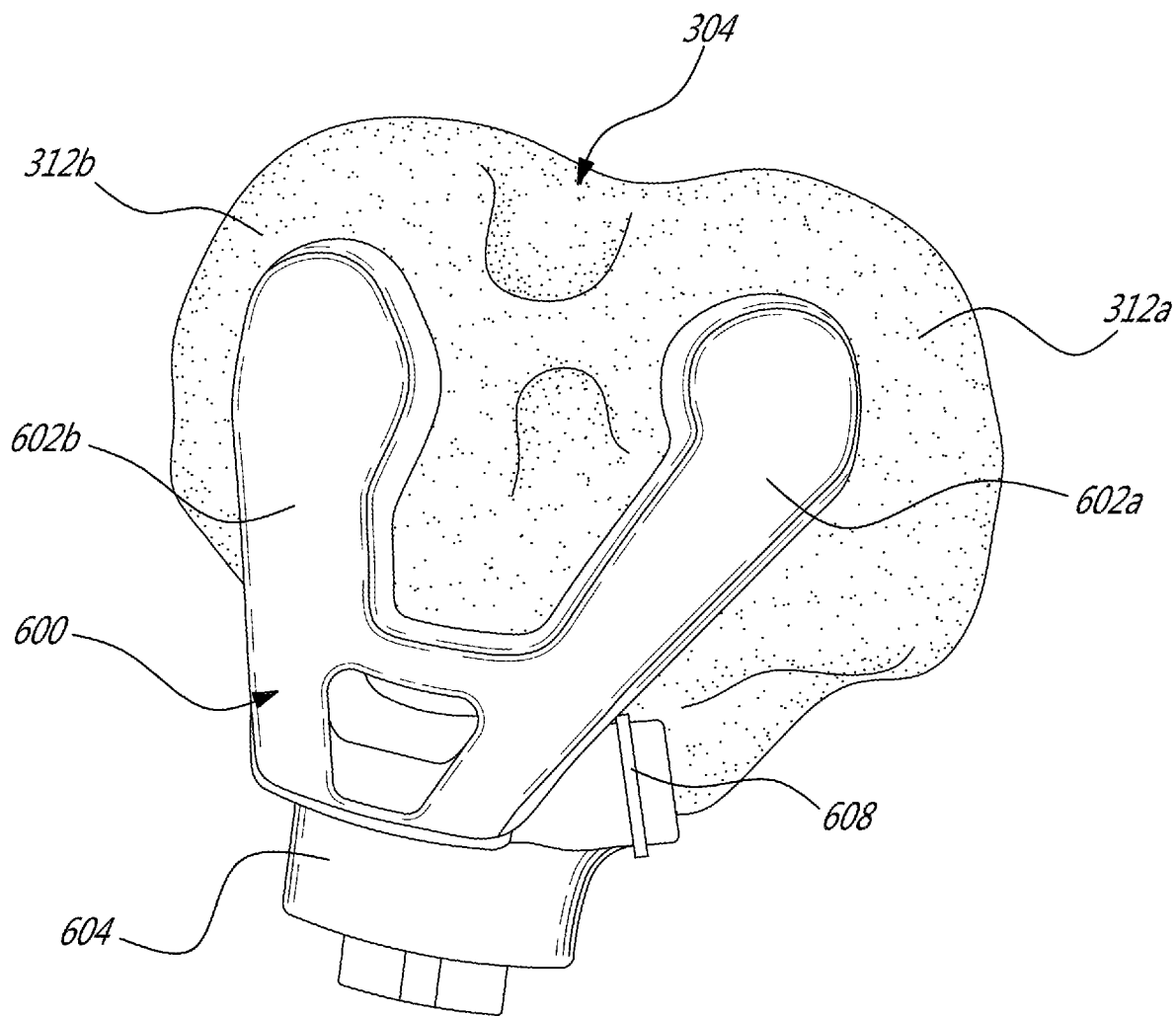
Figure 11C:
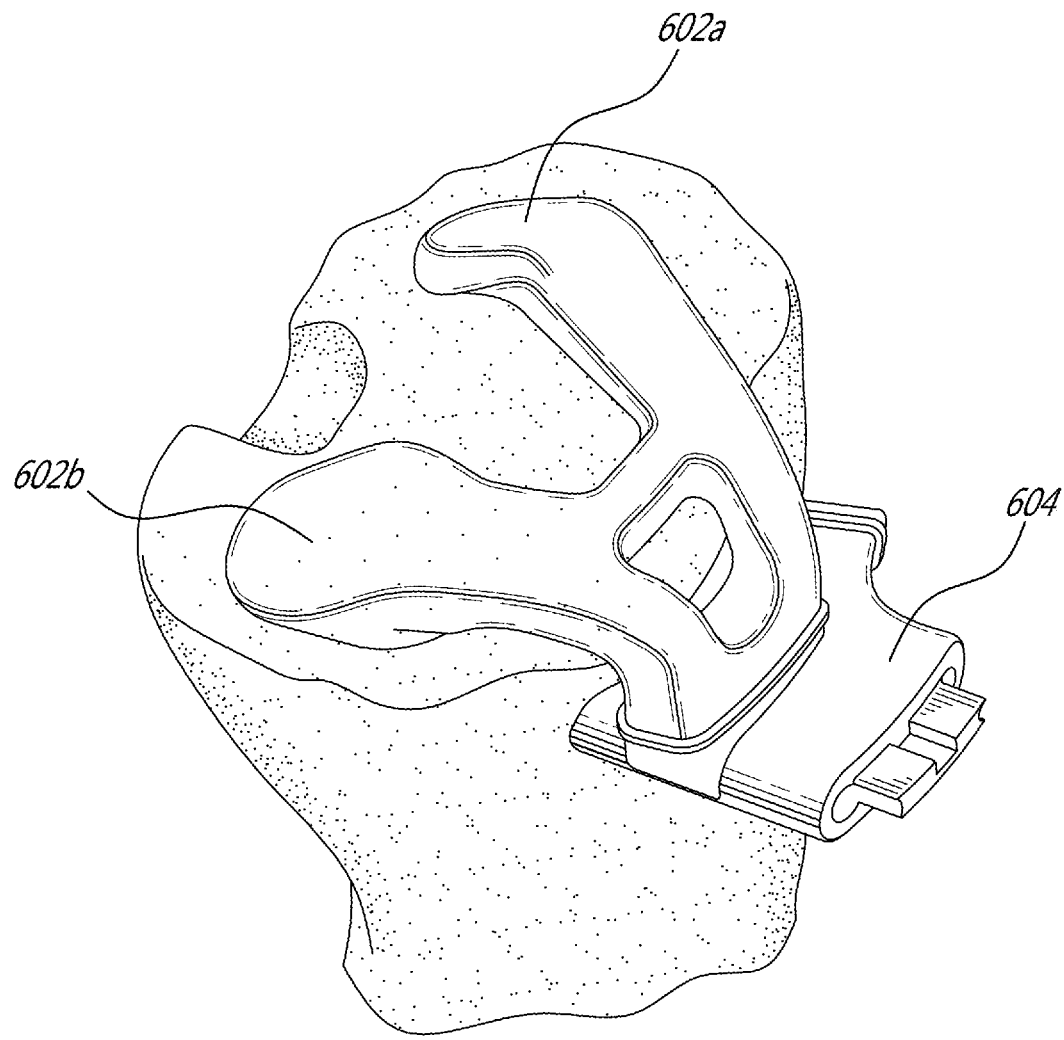

FIG. 11a and FIG. 11b illustrate an alternate embodiment 600 of the tibial jig 400 shown in FIG. 8. In this embodiment, the tibial jig 600 comprises a pair of attachment arms 602a and 602b each having a surface contacting portion (not shown) so that the arms 602a, 602b may respectively make contact with the articular surfaces (not shown) of the medial tibial plateau 312a and of the lateral tibial plateau 312b. A tibia contacting portion 604 is positioned adjacent an upper portion of the tibia 304 and comprises elongated guide bores 606a and 606b adapted to receive fixations for securing the tibial jig 600 to the tibia 304. A line indicator 608 may further be provided on the tibial jig 600 adjacent the tibia contacting portion 604. Proper positioning of the tibial jig 600 relative to the tibia 304 may be confirmed by alignment of the indicator 608 with the tibial tuberosity (not shown). Patient-specific modeling may be used to determine the position of the indicators 511, 514a, 514b, and the pointer 512 on the femoral jig 500 as well as the position of the indicator 608 on the tibial jig 600.

Use of the femoral jigs 200, 500 and the tibial jigs 400, 600 advantageously decreases errors and enables more precise prosthesis placement compared to traditional mechanical jigs. In addition, fewer instruments need to be sterilized for use during the surgical procedure. For instance, the use of patient-specific jigs as in 200, 400, 500, or 600 precludes the need for inserting rods through the intramedullary canal of the bone during the arthroplasty procedure. This in turn reduces the risk of perioperative fat embolism syndrome. Moreover, the use of patient-specific jigs as in 200, 400, 500, or 600 further allows for smaller incisions to be made in the patient's body, thus facilitating completion of minimally invasive surgery and allowing the prosthesis to more quickly restore the patient's joint to a generally pre-deteriorated state.

Figure 12:
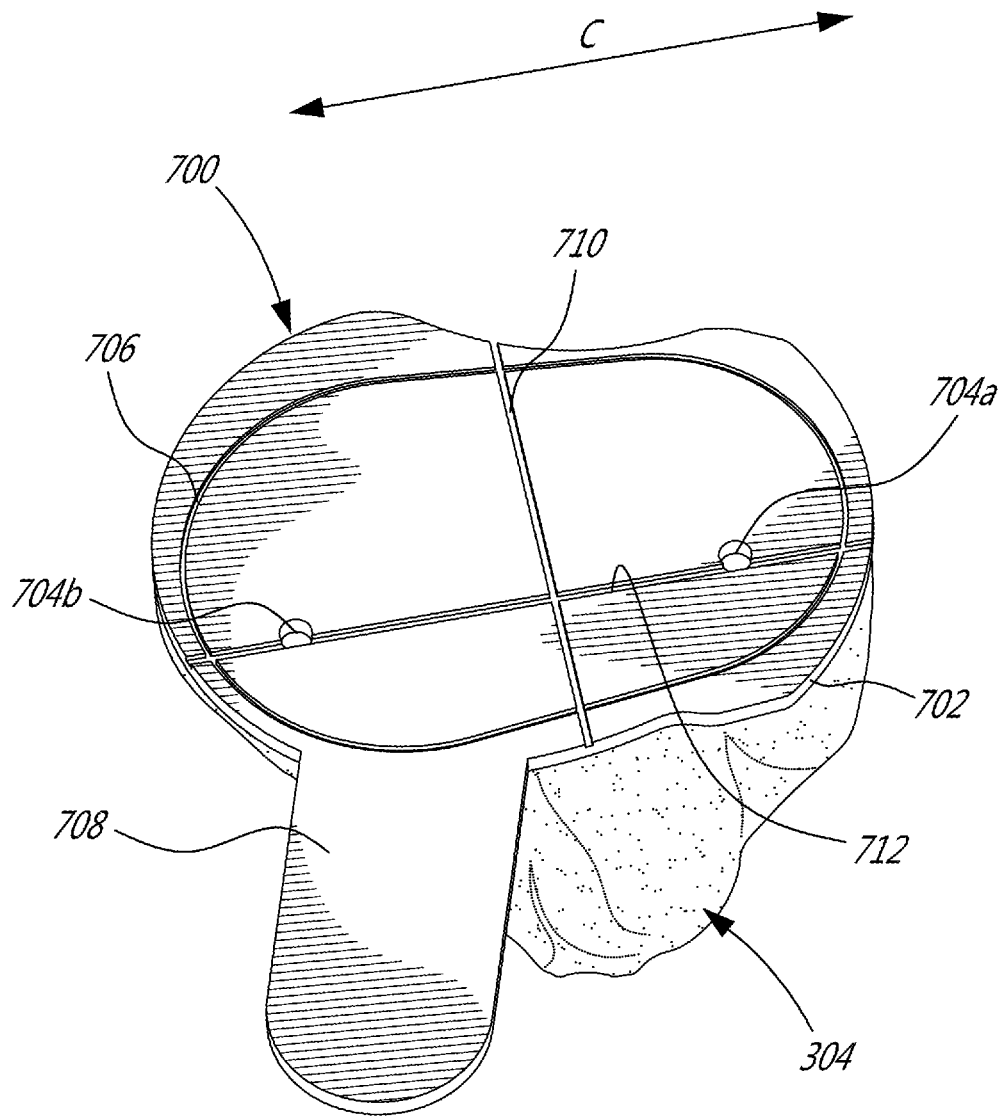
FIG. 12 is a front perspective view of a patient-specific tibial plate in accordance with the present disclosure.

Referring now to FIG. 12, a patient-specific plate 700 may be placed over the resected portion of the tibia 304 for guiding the position and/or rotation of the sizing plate as in 324 over the resected bone area. For this purpose, a contour 702 of the plate 700 may be designed so as to closely follow a contour of the tibial cut. Apertures as in 704a and 704b may further be machined into the plate 700 for guiding the user as to where in the tibia 304 holes should be drilled so as to receive fixations of the sizing plate 324, thereby attaching the latter to the tibia 304.

In order to ensure a proper fit of the tibial tray (not shown) on the resected portion of the tibia 304, and accordingly a proper positioning of the prosthesis, an outline or contour 706 of the tibial tray may be etched or otherwise delineated onto an upper surface 708 of the plate 700. Such a contour 706 may be obtained as a result of the user's pre-operative planning, during which the size and shape of the prosthesis best-suited to the patient's anatomy has been selected. In addition, a first axis 710 substantially parallel to the anterior-posterior direction A and a second axis 712 substantially parallel to the medio-lateral direction C may be machined on the surface 708 of the plate 700. In this manner, while placing the tibial tray on the resected portion of the tibia 304, a user may verify a proper alignment thereof relative to the axes 710 and 712, thereby ensuring proper positioning of the prosthesis. It should be understood that additional alignment features as well as other indications, such as the size and model of the prosthesis component, may also be shown on the surface 708.

Referring to FIGS. 13a to 13d, a patient-specific rotational guide 800 may be used as an alternative to the patient-specific plate 700 to ensure proper positioning and rotation of the sizing plate 324 on the resected portion of the tibia (not shown). The rotational guide 800 illustratively comprises a tray attachment member 802 for coupling the rotational guide 800 to the sizing plate 324. The rotational guide 800 may further comprise a bone contacting member 804 for contacting a bone the sizing plate 324 is to be mated with, the bone contacting member 804 being produced by patient-specific fabrication using bone imaging. Although a tibial sizing plate 324 has been shown for illustrative purposes, it should be understood that the rotational guide 800 may be adapted for use on a bone other than the tibia, for example on the distal portion of a femur (not shown). It should also be understood that the rotational guide 800 may be used with a variety of jig types as well as for repair of various articular joints other than the knee.

The tray attachment member 802 may be coupled to the sizing plate 324 using suitable attachment means (not shown). For instance, the tray attachment member 802 may be clipped to a plate handle 806 coupled to the sizing plate 324. It should be understood that other means of securing the tray attachment member 802 of the rotational guide 800 to the sizing plate 324 may apply.

Figure 13A:
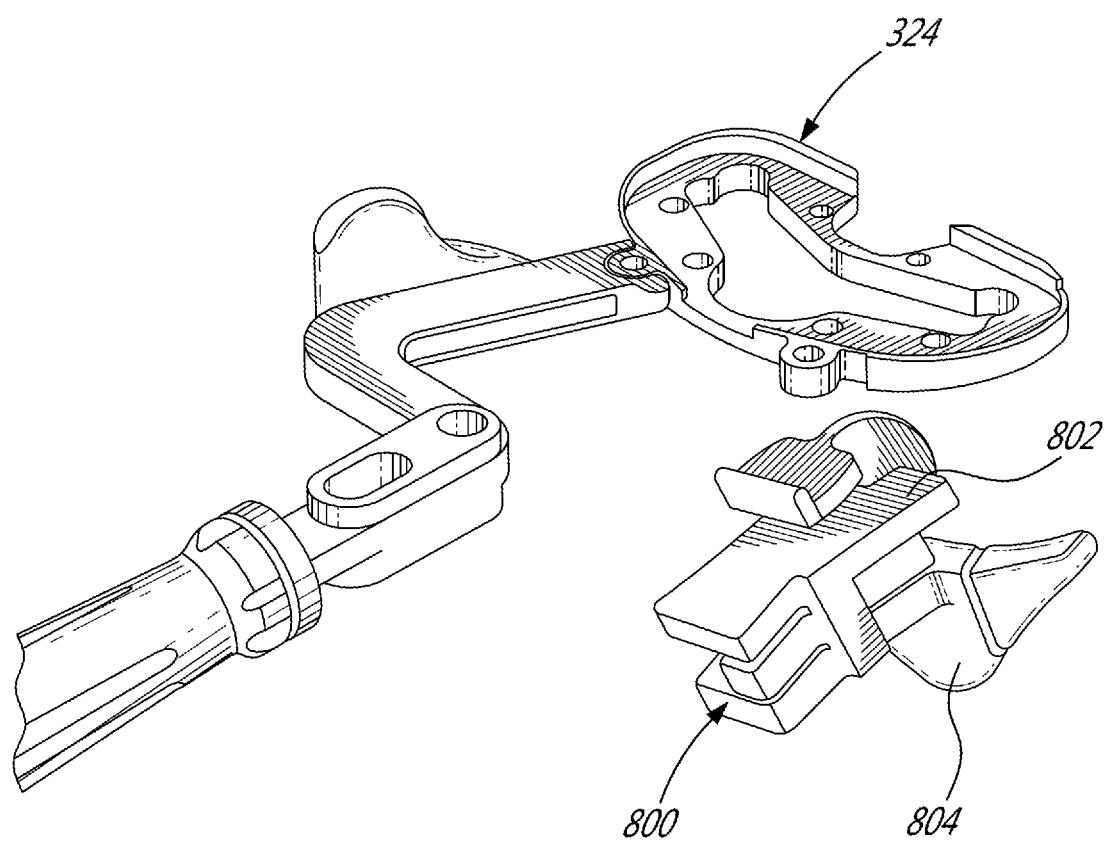
FIG. 13a is a perspective view of a rotational guide and of a sizing plate coupled to a plate handle in accordance with a first embodiment of the present disclosure.
Figure 13B:
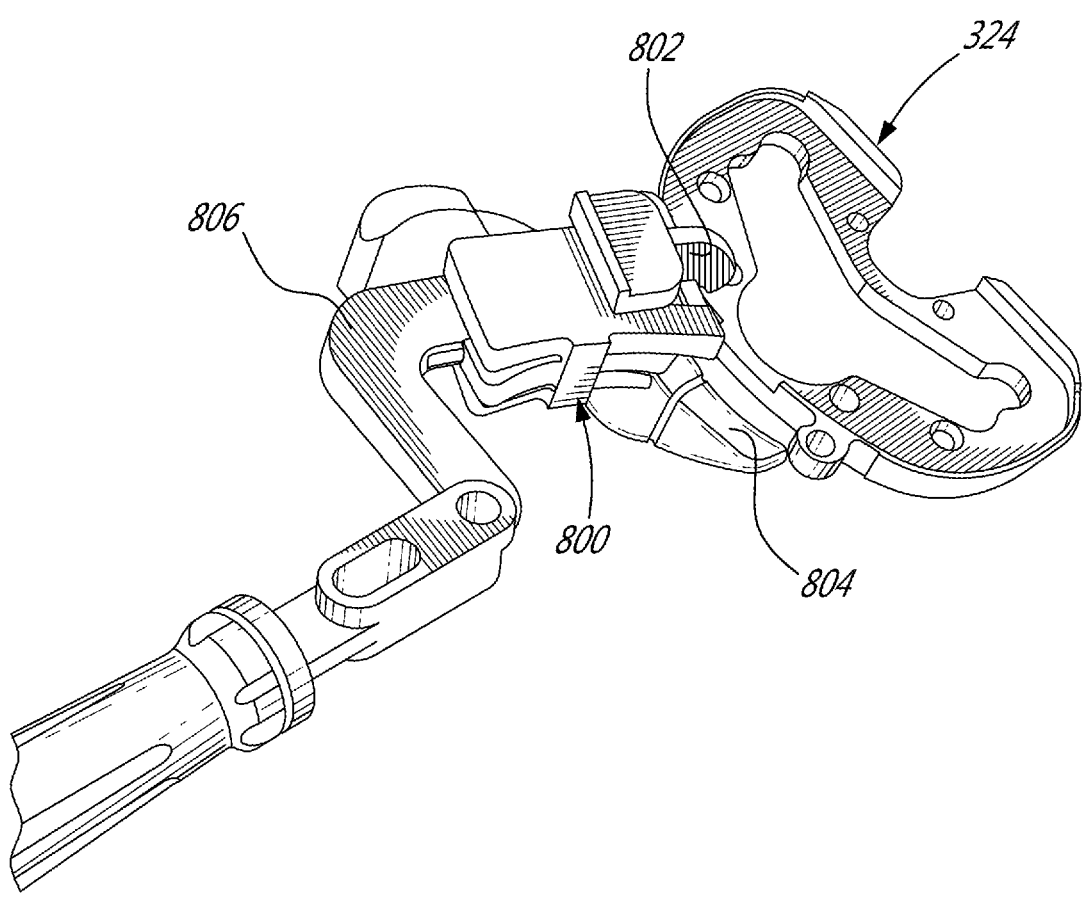
FIG. 13b is a perspective view of the rotational guide of FIG. 13a coupled to the plate handle and sizing plate.
Figure 13C:
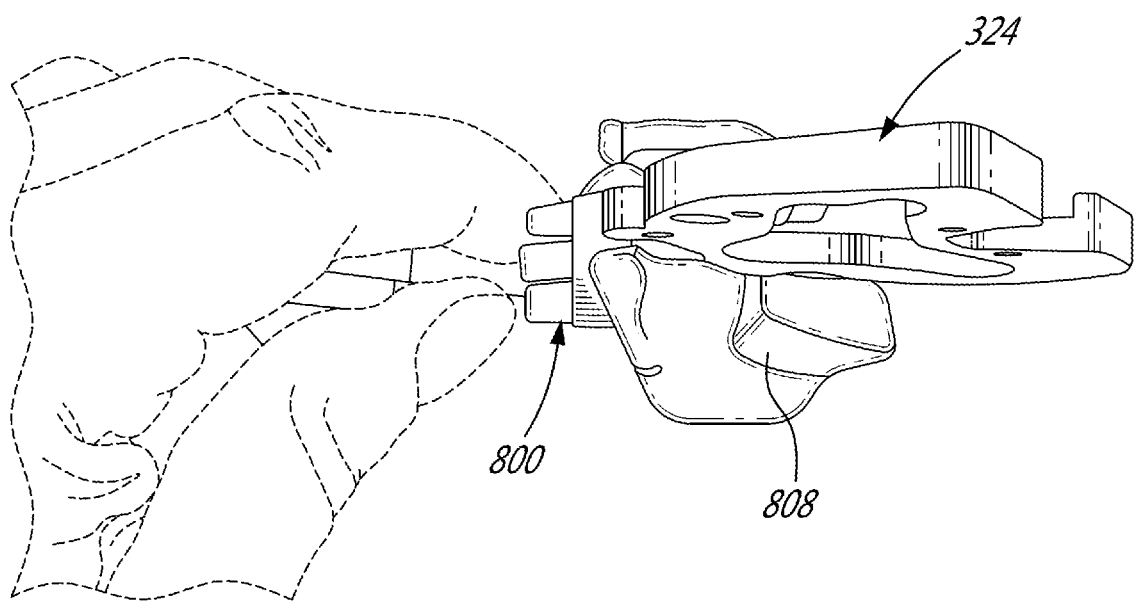
FIG. 13c is a side view of the rotational guide of FIG. 13b.
Figure 13D:
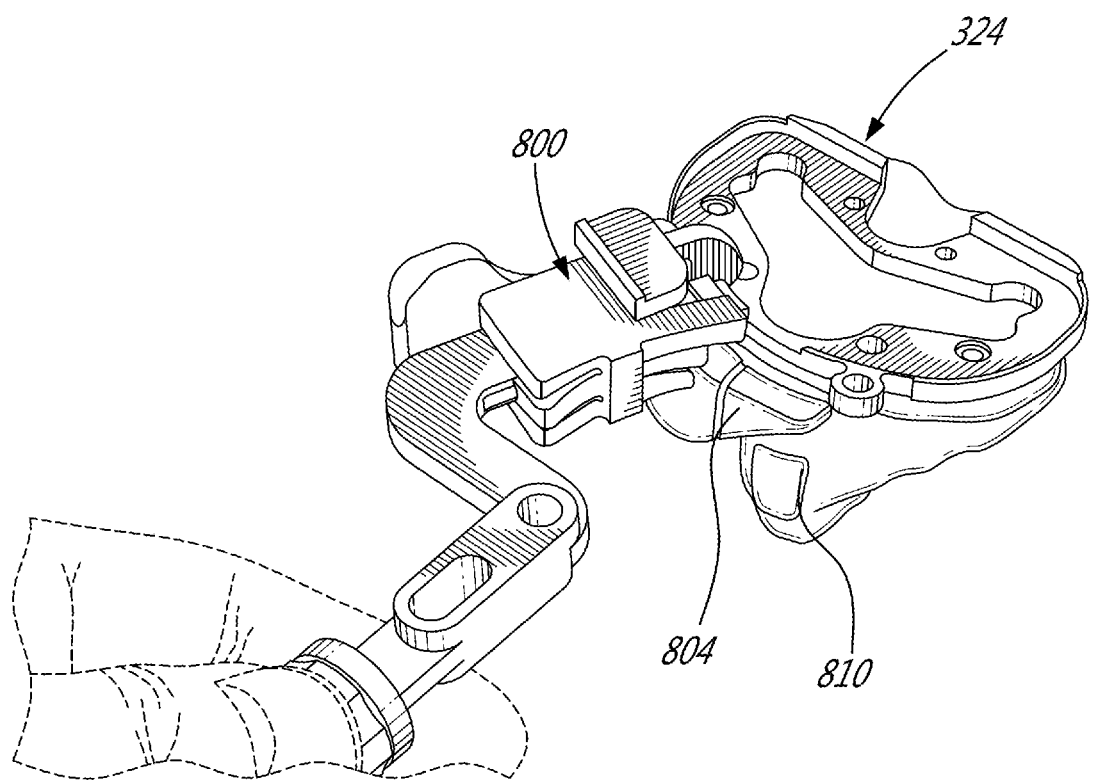
FIG. 13d is a perspective view of the rotational guide of FIG. 13c mated with a bone surface in accordance with a first embodiment of the present disclosure.
Figure 13E:
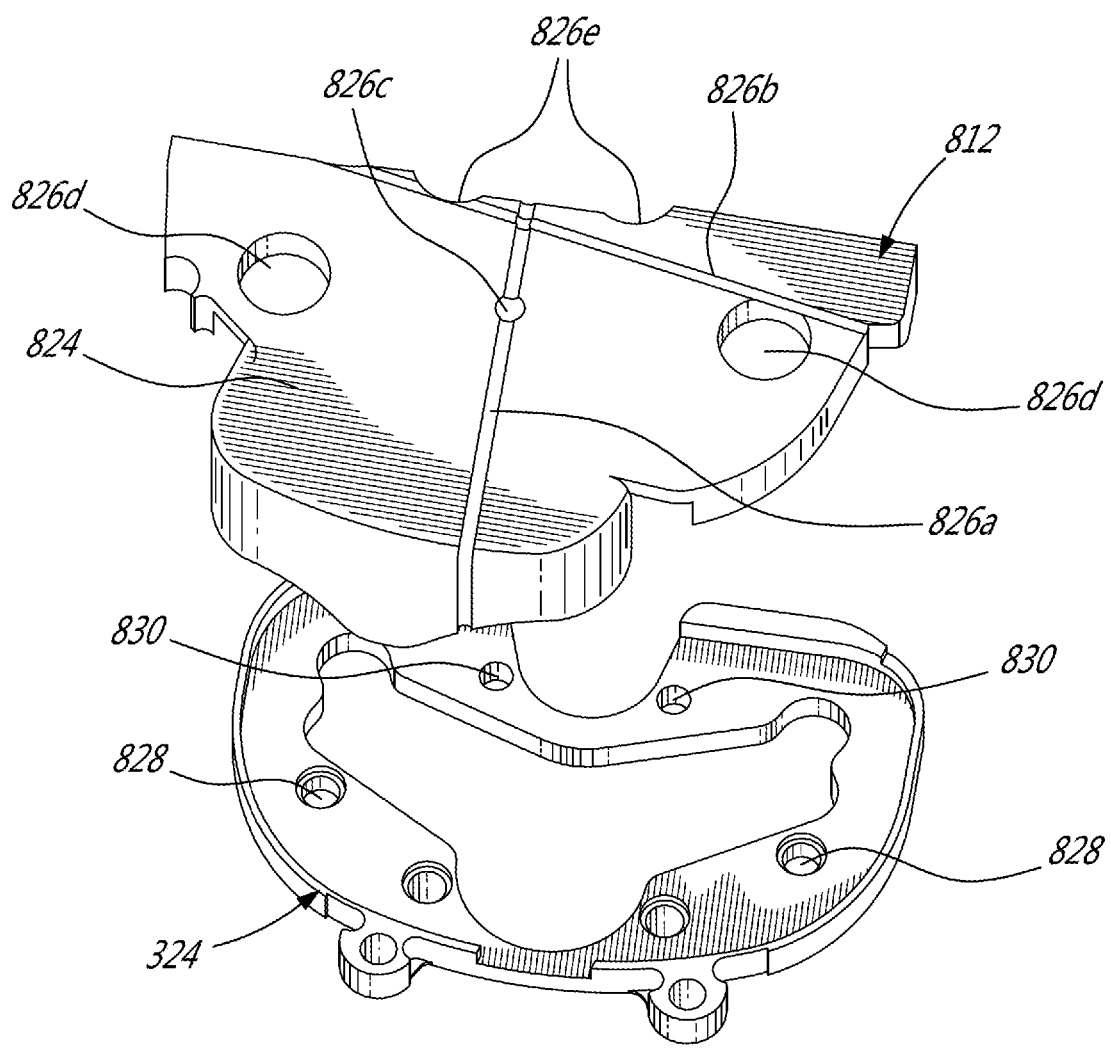
FIG. 13e is a perspective view of a rotational guide and of a sizing plate in accordance with a second embodiment of the present disclosure.
Figure 13F:
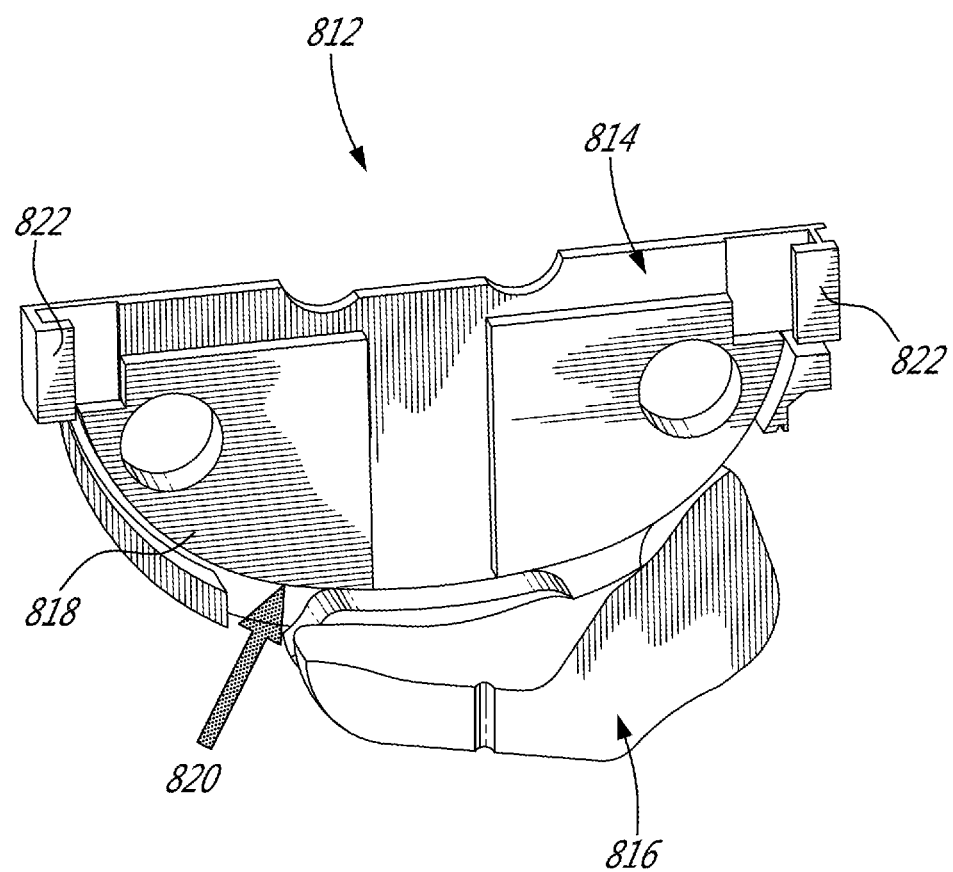
FIG. 13f is a bottom perspective view of the rotational guide of FIG. 13e.
Figure 13G:
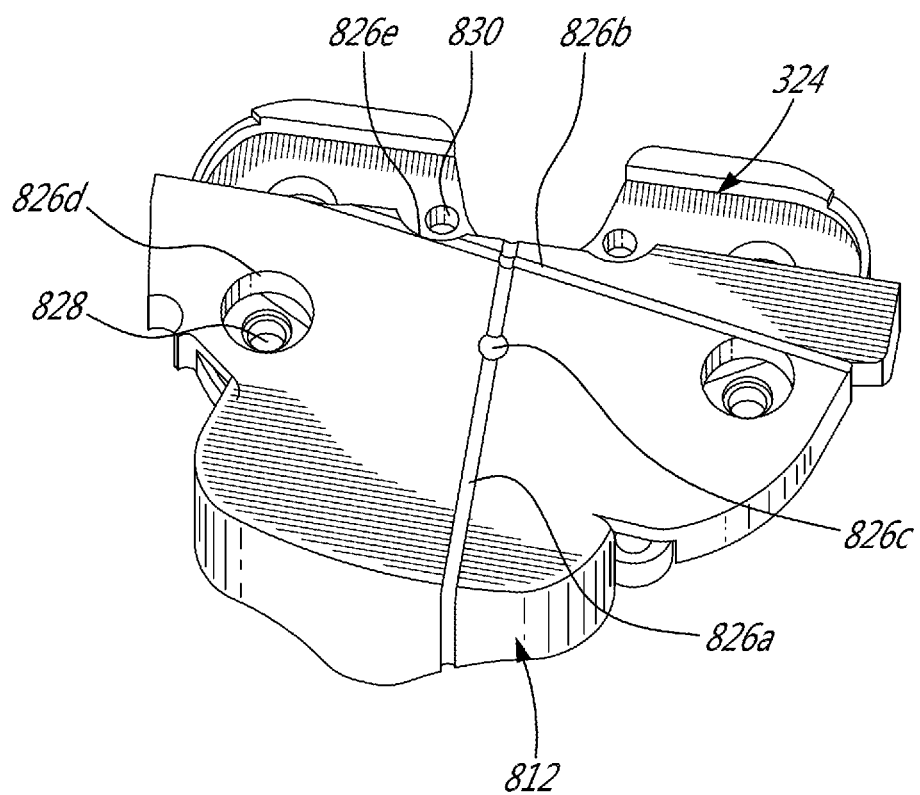
FIG. 13g is a top perspective view of the rotational guide of FIG. 13e coupled to the sizing plate.
Figure 13H:
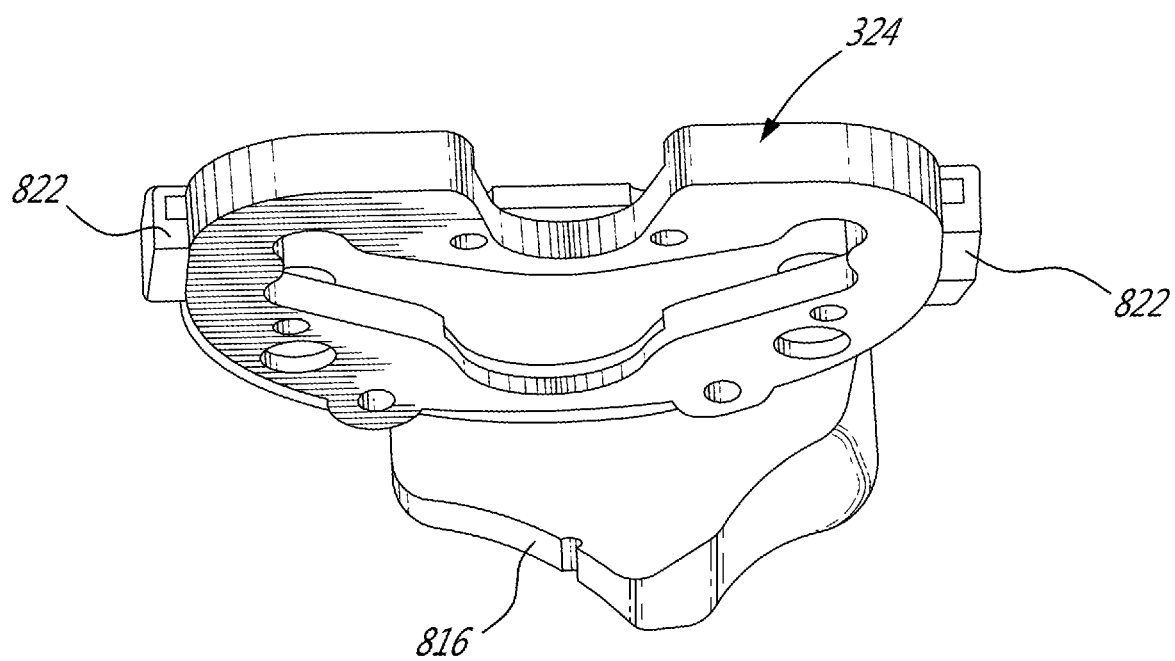
FIG. 13h is a bottom perspective view of the rotational guide and sizing plate of FIG. 13g.

As shown in FIG. 13c and FIG. 13d, the bone contacting member 804 may comprise a PSI bone contacting surface 808 adapted to mate with a corresponding bone surface 810 of the bone the sizing plate 324 is to be positioned on. The bone contacting member 804 is designed so that the bone contacting surface 808 precisely matches a geometry of the bone surface 810. For this purpose, the bone contacting member 804, and more particularly the bone contacting surface 808, may be manufactured from image data of the patient's anatomy obtained during pre-operative planning, as discussed above. In this manner, accurate positioning of the sizing plate 324 relative to the bone surface 810 may be achieved.

Referring to FIGS. 13e to 13h, a patient-specific rotational guide 812 in accordance with another embodiment will now be described. The rotational guide 812 comprises a tool attachment member 814 configured to secure the rotational guide 812 to a tool, such as the bone sizing plate 324. The rotational guide 812 further comprises a bone attachment member 816 having a mating surface (not shown) configured to contact a bone (not shown) the tool is mated with. The mating surface is illustratively shaped so as to conform to a shape of the bone surface the bone attachment member 816 is mated with.

In one embodiment, the tool attachment member 814 has a contour (not shown) conforming to the perimeter (not shown) of the tool. The tool attachment member 814 further has a lower surface 818 adapted to mate with the tool. For this purpose, an inner contour 820 of the lower surface 818 is configured so as to conform to a shape of the tool. In this manner, the rotational guide 812 can be retained in position relative to the tool when the rotational guide 812 is secured thereto. The lower surface 818 is further provided with attachment means 822, such as clipping means, that enable attachment of the rotational guide 812 to the tool. In one embodiment, the attachment means 822 comprise a first and a second clipping means that allow the rotational guide 812 to be clipped to the tool. It should be understood that any other suitable attachment means may be provided.

An upper surface 824 of the rotational guide 812 is illustratively provided with one or more alignment elements as in 826a, 826b, 826c, 826d, and 826e used for confirming the pre-operative planning intra-operatively. The alignment elements as in 826a, 826b, 826c, 826d, and 826e may further be used for guiding the positioning of the tool on the resected bone surface. In particular, the alignment element 826a may be an anterior-posterior line formed on the upper surface 824 and indicative of an anterior-posterior direction of the bone. The alignment element 826b may be an medio-lateral line formed on the upper surface 824 and indicative of a medio-lateral direction of the bone. The alignment element 826c may be indicative of a direction of the mechanical axis of the bone. It should be understood that other anatomical directions may apply. The alignment elements as in 826d may comprise openings adapted to cooperate with apertures as in 828 formed in the tool, e.g. the bone sizing plate 324. In particular, when the rotational guide 812 is coupled to the plate 324, the alignment elements 826d may be aligned with the apertures 828 to enable fixations (not shown) to be received in the apertures 828 for securing the plate 324 on the resected surface. The alignment elements 826e may comprise cutouts formed in the tool attachment member 814 and adapted to cooperate with apertures as in 830 of the tool, e.g. the bone sizing plate 324. When rotational guide 812 is coupled to the plate 324, the alignment elements 826e may also be aligned with the apertures 830 to enable fixations, such as a screws or the like, to be received in the apertures 830.

FIG. 14a, FIG. 14b, and FIG. 14c show and illustrative embodiment of a cut slot 900 for use with at least one of the above-mentioned tibial and femoral jigs. It should be understood that the tibial and femoral jigs may or may not comprise such a cut slot 900 and that the cut slot 900 may be used with non PSI tools. In addition, the cut slot 900 may be provided as a disposable tool for use with disposable instruments, such as disposable cut guides.

The cut slot 900 illustratively comprises a first member 902 and a second member 904 each comprising opposite ends as in $906_1$, $906_2$. Each one of the members, e.g. member 902, is provided at the ends thereof, e.g. ends $906_1$, with an attachment means, e.g. attachment means $908_1$, adapted to cooperate with the corresponding attachment means, e.g. attachment means $908_2$, provided at the ends, e.g. ends $906_2$, of the other member, e.g. member 904. When so coupled to one another, the first and second members 902, 904 define therebetween a spacing 910 adapted to receive therein a saw blade (not shown) used to execute pre-planned bone cuts. In the illustrated embodiment, the attachments means $908_1$, $908_2$ are adapted to be snap-fitted together. It should be understood that other attachment means configurations may also apply. It should also be understood that the attachment means $908_1$, $908_2$ may be provided at a single one of the ends $906_1$, $906_2$ of each member 902, 904 rather than at both ends $906_1$, $906_2$ thereof.

The cut slot 900 is illustratively metallic and the members 902, 904 may be made of a stamped sheet of metal. It should be understood that a variety of manufacturing processes may be used for the cut slot 900. For example, the members 902, 904 may be machined, formed, or the like. Still, regardless of the manufacturing process used, it is desirable for the cut slot 900 to have a substantially constant width along a length thereof.

Figure 14D:
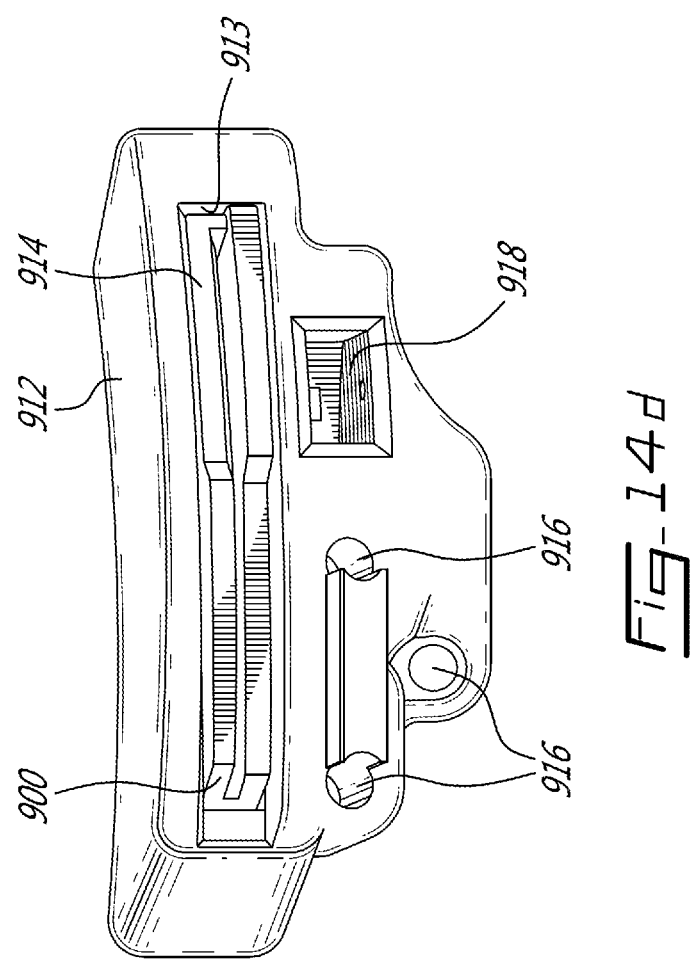
FIG. 14d is a perspective view of the cut slot of FIG. 14a inserted into a cut guide in accordance with the present disclosure.
Figure 14E:
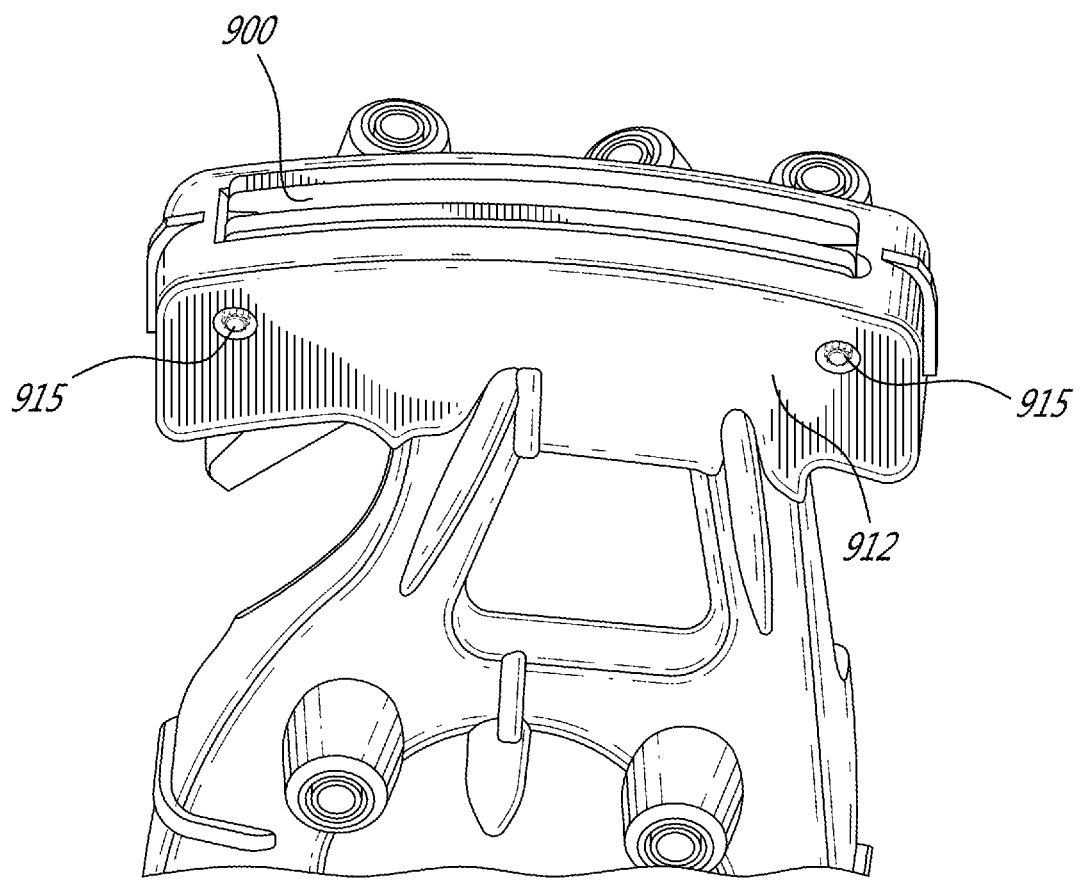
FIG. 14e is a perspective view of the cut slot of FIG. 14d showing assembly pins in accordance with the present disclosure.
Figure 14F:
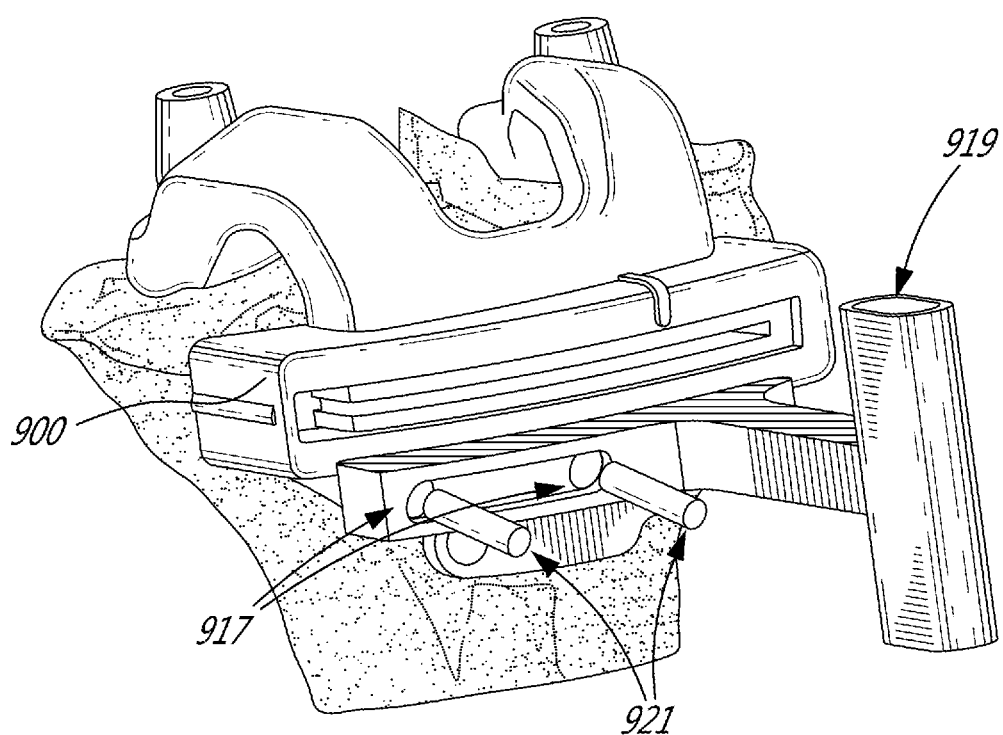
FIG. 14f is a perspective view of the cut slot of FIG. 14e receiving a drop rod adaptor in accordance with the present disclosure.

Referring now to FIG. 14d, FIG. 14e, and FIG. 14f, the cut slot 900 may be inserted into a housing 912, such as a cut guide housing. The housing 912 may be made of plastic or any other suitable material. The cut slot 900 may be press-fitted into an elongate opening 913 machined into the housing 912. For this purpose, the first and second members (references 902, 904 of FIG. 14a) may be shaped to fit the size of the opening 913. A lip 914 may further be formed in each one of the first and second members 902, 904 so as to guide, and accordingly facilitate, the insertion of the saw blade into the spacing (reference 910 in FIG. 14b). Assembly pins 915 may then be used to retain the cut slot 900 within the housing 912. The housing 912 may further comprise a plurality of apertures as in 916 for receiving therein bushings 917 (see FIG. 14f) as well as a receptor 918 for a drop rod adaptor 919 (see FIG. 14θ). In one embodiment, the bushings 917 are press-fitted into plastic. The bushings may be adapted to accommodate the drill bit of the surgical drill guide (not shown) and may be used to prevent residual plastic shavings or other debris resulting from the drilling process. The bushings 917 may also be used to secure the cut slot 900 on the bone during cutting. In particular, a locking bushing (not shown) may be provided to stabilize the cut slot 900, and accordingly the tibial or femoral jig the cut slot 900 is coupled to, during the cutting procedure. Accurate positioning of the cut slot 900 relative to the bone may then be achieved.

As seen in FIG. 14f, the drop rod adaptor 919 may be aligned with two anterior medial bushings 917 for accurately positioning the drop rod adaptor 919 in varus-valgus as well as ensuring proper rotation of the drop rod adaptor 919 relative to the cut slot 900. The drop rod adaptor 919 may be further stabilized by a ball plunger (not shown) provided thereon. When the drop rod adaptor 919 is inserted into the receptor 918, the ball plunger may indeed be retained within an aperture (not shown) formed in the receptor 918. The drop rod 919 may further be provided with apertures adapted to cooperate with the bushings 917 for receiving pins as in 921. Pinning can then be performed while the drop adaptor 919 is in place relative to the cut slot 900.

Referring to FIG. 14g, in order to provide accuracy and stability to the positioning of the cut slot 900 relative to the housing 912, the latter illustratively has formed therein a pair of inferior crush ribs 920a and a pair of lateral crush ribs 920b. It should be understood that any other suitable number of crush ribs 920a, 920b may be used. The crush ribs 920a and 920b ensure that the cut slot 900 is stable as well as account for tolerance variations between the metallic cut slot 900 and the plastic housing 912.

The inferior crush ribs 920a are illustratively positioned adjacent a lower surface (not shown) of the second member 904. The lateral crush ribs 920b are respectively positioned adjacent the edge (reference $906_1$ in FIG. 14a) of the first member 902 and the edge (reference $906_2$ in FIG. 14b) of the second member 902. Other suitable configurations may apply. The crush ribs 920a and 920b may be made of resilient or other suitable material, such as plastic, so as to allow the cut slot 900 to be press-fitted within the housing 912. In particular, each crush rib 920a or 920b illustratively comprises a base portion (not shown) secured to the housing 912 and a deformable portion (not shown) extending away from the base portion and into the opening (reference 913 in FIG. 14d) formed in the housing 912. When the cut slot 900 is inserted into the opening 913, the cut slot 900 comes into contact with the deformable portion of the crush ribs 920a and 920b. The deformable portion is then crushed, bent, or otherwise deformed or deflected as a result of the pressure exerted thereon by the cut slot 900 during insertion. As a result, the cut slot 900 is then securely retained within the opening 913.

The embodiments of the invention described above are intended to be exemplary. Those skilled in the art will therefore appreciate that the foregoing description is illustrative only, and that various alternate configurations and modifications can be devised without departing from the spirit of the present invention. Accordingly, the present invention is intended to embrace all such alternate configurations, modifications and variances which fall within the scope of the appended claims.

The invention claimed is:

1. An assembly for resecting an articular bone surface in an articular joint repair procedure comprising:
   a housing adapted to be positioned adjacent the articular bone surface, the housing having an opening defined therein; and
   an insert adapted to be fitted into the opening, the insert including a first member and a second member separate from and releasably coupled to the first member in a releasably coupled configuration, wherein at least one of the first member and the second member is sheet metal having a bent portion at an end thereof, ends of the first member and of the second member contacting each other in the releasably coupled configuration, the releasably coupled configuration of the first member and of the second member defining an aperture with a substantially constant width by spacing the first member from the second member, the aperture adapted to receive a saw blade for resecting the articular bone surface.

2. The assembly of claim 1, wherein the first member and the second member each have a first end and a second end opposite the first end and are each provided with a first attachment at the first end and with a second attachment at the second end, the first attachment of the first member adapted to cooperate with the first attachment of the second member and the second attachment of the first member adapted to cooperate with the second attachment of the second member for coupling the first member to the second member in the releasably coupled configuration, the first attachment of the first member adapted to cooperate with the first attachment of the second member and the second attachment of the first member adapted to cooperate with the second attachment of the second member for coupling the first member to the second member to ensure the substantially constant width of the aperture.

3. The assembly of claim 2, wherein the housing comprises at least one crush rib for securing a position of the insert within the opening, the at least one crush rib adapted to be resiliently deformed in response to a pressure being exerted thereon as the insert is fitted into the opening.

4. The assembly of claim 3, wherein the housing comprises a first, a second, a third, and a fourth crush rib and further wherein, with the insert fitted into the opening, the first crush rib is positioned adjacent the first end of the first member, the second crush rib is positioned adjacent the first end of the second member, and the third and fourth crush ribs are positioned adjacent a lower surface of the second member.

5. The assembly of claim 2, wherein the first attachment and the second attachment are snap-fits.

6. The assembly of claim 1, wherein the first and second members are made of a stamped sheet of metal.

7. The assembly of claim 6, wherein the housing is made of a plastic material.

8. The assembly of claim 6, wherein the first member and the second member each have a first end and a second end opposite the first end and are each provided with a first attachment in the sheet metal at the first end and with a second attachment in the sheet metal at the second end, the first attachment of the first member adapted to cooperate with the first attachment of the second member and the second attachment of the first member adapted to cooperate with the second attachment of the second member for coupling the first member to the second member, whereby the first member and the second member are releasably connected only by way of the sheet metal of the first member and of the second member.

9. The assembly of claim 1, wherein the housing defines a receptor.

10. The assembly of claim 9, including a rod configured to be received in the receptor.

11. The assembly of claim 1, wherein the housing is a patient specific jig including at least one bone contacting member adapted to contact a bone, the at least one bone contacting member having at least one mating surface shaped using patient-specific modeling to conform to a shape of the bone, the at least one mating surface adapted to matingly contact a portion of the bone, the patient specific jig further including at least two drill bores configured for guiding a placement of pins in the bone wherein a positioning of the at least two drill bores in the patient specific jig is as a function of patient-specific modeling and of a geometry of the aperture for the articular bone surface to be located at a planned location.

12. The assembly of claim 11, further including a patient-specific model including a geometry of the patient-specific jig relative to the bone and including the at least one bone contacting member and the at least two drill bores corresponding to a planned mating contact between the patient-specific jig and to a planned planar resected surface aligned with the aperture.

13. The assembly of claim 11, wherein the at least one bone contacting member has formed therein at least one clearance shaped as a function of a shape of at least one selected area of the articular surface for preventing contact between the at least one mating surface and the at least one selected area.

14. The assembly of claim 13, wherein the at least one clearance is shaped to prevent contact between the at least one mating surface and at least one of cartilage, soft tissue, osteophytes, and menisci.

15. The assembly of claim 1, wherein the first member has the bent portion at both of its ends, and the second member is without the bent portion.

16. The assembly of claim 15, wherein attachments means at the ends of the first member and the second member are cooperating tab and grooves.

17. The assembly of claim 16, wherein the cooperating tab and grooves are made of sheet metal.

* * * * *